US009023774B2

(12) United States Patent
Mullen et al.

(10) Patent No.: US 9,023,774 B2
(45) Date of Patent: May 5, 2015

(54) KETAL COMPOUNDS AND USES THEREOF

(71) Applicant: SEGETIS, Inc., Golden Valley, MN (US)

(72) Inventors: Brian D. Mullen, Delano, MN (US);
Chunyong Wu, Plymouth, MN (US);
Tara J. Mullen, Delano, MN (US);
Marc D. Scholten, Saint Paul, MN (US);
Vivek Badarinarayana, St. Louis Park, MN (US)

(73) Assignee: SEGETIS, Inc., Golden Valley, MN (US)

( * ) Notice: Subject to any disclaimer, the term of this patent is extended or adjusted under 35 U.S.C. 154(b) by 86 days.

(21) Appl. No.: 13/950,032

(22) Filed: Jul. 24, 2013

(65) Prior Publication Data

US 2013/0310288 A1    Nov. 21, 2013

Related U.S. Application Data

(63) Continuation of application No. 13/333,273, filed on Dec. 21, 2011, now abandoned, which is a continuation of application No. PCT/US2010/039554, filed on Jun. 22, 2010.

(60) Provisional application No. 61/219,098, filed on Jun. 22, 2009.

(51) Int. Cl.
| | |
|---|---|
| *C07D 319/06* | (2006.01) |
| *C10M 129/20* | (2006.01) |
| *C07D 407/12* | (2006.01) |
| *C07D 317/30* | (2006.01) |
| *C08K 5/1515* | (2006.01) |
| *C08K 5/1565* | (2006.01) |
| *C08K 5/1575* | (2006.01) |
| *C10M 129/70* | (2006.01) |

(52) U.S. Cl.
CPC ........... *C07D 407/12* (2013.01); *C10M 129/20* (2013.01); *C10M 2207/044* (2013.01); *C07D 317/30* (2013.01); *C08K 5/1515* (2013.01); *C08K 5/1565* (2013.01); *C08K 5/1575* (2013.01); *C10M 129/70* (2013.01)

(58) Field of Classification Search
USPC ................................... 508/308, 370; 549/370
See application file for complete search history.

(56) References Cited

U.S. PATENT DOCUMENTS

| | | | |
|---|---|---|---|
| 1,934,309 A | 11/1933 | Hoover | |
| 2,004,115 A | 6/1935 | Izard | |
| 2,260,261 A | 10/1941 | Morey et al. | |
| 2,556,135 A | 6/1951 | Croxall et al. | |
| 2,654,723 A | 10/1953 | Greene | |
| 2,985,536 A | 5/1961 | Stein et al. | |
| 3,201,420 A | 8/1965 | Fuzesi et al. | |
| 3,330,840 A | 7/1967 | Pryde et al. | |
| 3,658,789 A | 4/1972 | Fried | |
| 3,714,202 A | 1/1973 | Nakaguchi et al. | |
| 3,855,248 A | 12/1974 | Lannert et al. | |
| 4,153,064 A | 5/1979 | Sawada et al. | |
| 4,465,866 A | 8/1984 | Takaishi et al. | |
| 4,737,426 A * | 4/1988 | Roth | 430/17 |
| 4,792,411 A | 12/1988 | Walsh | |
| 4,806,448 A | 2/1989 | Roth | |
| 5,013,543 A | 5/1991 | Mercado et al. | |
| 5,028,667 A | 7/1991 | McLain et al. | |
| 5,093,111 A | 3/1992 | Baker et al. | |
| 5,095,098 A | 3/1992 | McLain et al. | |
| 5,202,413 A | 4/1993 | Spinu et al. | |
| 5,208,297 A | 5/1993 | Ford et al. | |
| 5,210,108 A | 5/1993 | Spinu et al. | |
| 5,266,592 A | 11/1993 | Grub et al. | |
| 5,289,384 A | 2/1994 | Akiyama | |
| 5,292,859 A | 3/1994 | Ford et al. | |
| 5,705,087 A | 1/1998 | Mushrush et al. | |
| 5,917,059 A | 6/1999 | Bruchmann et al. | |
| 5,998,092 A | 12/1999 | McCulloch et al. | |
| 6,372,791 B1 | 4/2002 | Shapiro et al. | |
| 6,395,810 B1 | 5/2002 | Luitjes et al. | |
| 6,528,025 B1 | 3/2003 | Boesch et al. | |
| 6,627,181 B1 | 9/2003 | Busch, Jr. et al. | |
| 6,703,478 B2 | 3/2004 | Nakane et al. | |
| 6,806,392 B2 | 10/2004 | Boesch et al. | |
| 6,962,767 B2 | 11/2005 | Watanabe et al. | |
| 7,094,395 B1 | 8/2006 | Qu et al. | |
| 8,632,612 B2 * | 1/2014 | Yontz | 8/405 |

(Continued)

FOREIGN PATENT DOCUMENTS

| | | |
|---|---|---|
| CA | 1000285 | 11/1976 |
| DE | 3220035 A1 | 1/1983 |

(Continued)

OTHER PUBLICATIONS

STIC Search Report dated Jul. 5, 2013, 90 pages.
Black, Cline, et al., "The Solubility of Water in Hydrocarbons", The Journal of Chemical Physics, vol. 16, pp. 537-543 (1948).
Dias, Jerry Ray and Carl Djerassi, "Mass Spectrometry in Structural and Stereochemical Problems—CCXVI: Anomalous Cleavage Ions in Bifunctional Compounds Resulting from Participatative Interaction", Organic Mass Spectrometry, vol. 6, 385-406 (1972).
Kobayashi, Shigero, et al., "Sterochemistry of the 2,4-dimethyl-1-3-dioxolan-2-yl Radical", Chemistry Letters, 695-698 (1973).

(Continued)

*Primary Examiner* — James Goloboy
(74) *Attorney, Agent, or Firm* — Cantor Colburn LLP

(57) ABSTRACT

Various esterified alkyl ketal ester or hydroxyalkyl ketal ester products are useful as components of organic polymer compositions. The ketal esters are produced in certain transesterifications between alkyl ketal esters and/or hydroxyalkyl ketal esters and polyols, aminoalcohols, polyamines, and/or polycarboxylic acids. The products are excellent plasticizers for a variety of organic polymers, notable poly(vinyl chloride) plastisols. The products are also very good lubricants for many lubrication applications.

55 Claims, No Drawings

(56) References Cited

U.S. PATENT DOCUMENTS

| | | | |
|---|---|---|---|
| 8,889,890 | B2 | 11/2014 | Wicks et al. |
| 2003/0133895 | A1 | 7/2003 | China et al. |
| 2003/0167681 | A1 | 9/2003 | Delgado Puche |
| 2004/0010064 | A1 | 1/2004 | Harashina et al. |
| 2004/0018954 | A1 | 1/2004 | Su et al. |
| 2004/0024260 | A1 | 2/2004 | Winkler et al. |
| 2004/0167245 | A1 | 8/2004 | Chappelow et al. |
| 2005/0031576 | A1 | 2/2005 | McManus et al. |
| 2005/0101700 | A1 | 5/2005 | Riebel |
| 2006/0069230 | A1 | 3/2006 | Papisov |
| 2006/0134045 | A1 | 6/2006 | Cao et al. |
| 2006/0207037 | A1 | 9/2006 | Fadel et al. |
| 2006/0211855 | A1 | 9/2006 | Doring et al. |
| 2008/0124426 | A1* | 5/2008 | Kobler et al. ............... 426/2 |
| 2008/0233453 | A1 | 9/2008 | Shiba et al. |
| 2008/0242721 | A1 | 10/2008 | Selifonov |
| 2010/0087357 | A1 | 4/2010 | Morgan, III et al. |
| 2011/0196081 | A1 | 8/2011 | Kwon et al. |
| 2011/0300083 | A1 | 12/2011 | Yontz et al. |
| 2013/0053564 | A1 | 2/2013 | Selifonov et al. |

FOREIGN PATENT DOCUMENTS

| | | |
|---|---|---|
| DE | 10036423 A1 | 3/2001 |
| EP | 012543 A1 | 6/1980 |
| EP | 0308956 A2 | 3/1989 |
| EP | 0507190 A1 | 10/1992 |
| FR | 1445013 | 7/1966 |
| GB | 1151095 | 5/1969 |
| JP | 2800437 A | 9/1953 |
| JP | 4217972 | 8/1992 |
| JP | 2006143702 A | 6/2006 |
| SU | 722912 | 3/1980 |
| WO | 9412489 A1 | 6/1994 |
| WO | 2004099173 A1 | 11/2004 |
| WO | 2005097724 A1 | 10/2005 |
| WO | 2007062158 A2 | 5/2007 |
| WO | 2007094922 A2 | 8/2007 |
| WO | 2008089463 A2 | 7/2008 |
| WO | 2008098375 A1 | 8/2008 |
| WO | 2009032905 A1 | 3/2009 |
| WO | 2009048874 A1 | 4/2009 |
| WO | 2010036884 A1 | 9/2009 |
| WO | 2010027663 A1 | 3/2010 |
| WO | 2010151558 A1 | 12/2010 |
| WO | 2011047420 A1 | 4/2011 |

OTHER PUBLICATIONS

Doolittle, Arthur K., "Application of a Mechanistic Theory of Solvent Action to Plasticizers and Platicization", Journal of Polymer Science, vol. 2, No. 2 (1947) 121-141.

European Search Report for Application No. 10 792 584.4, dated Aug. 14, 2013, 4 pages.

Bulat, J.A., "A practical synthesis of cis-jasmone from levulinic acid", Canadian J. of Chem, 54, Dec. 15, 1976, p. 3869-3871.

Campbell, I.D., "The Hydration of Undeca-1,7-diyne", J. of Chemical Society, Jan. 1, 1964, 1092-1096.

Chinese Search Report for Application No. 2010800280426, from Department of Chemical Invention of Patent Examination Cooperation Center, Beijing, dated Mar. 30, 2013, 1 page.

Cross, Brian E. and Zammitt, Leslie J., "Part 111 Synthesis of a Methyl Ether of Bisdeoxyerythrostominone", J. Chemical Society, Perkins Transactions 1, No. 19, Jan. 1, 1975, pp. 1936-1941.

Doedens, Robert J., Transition-State Geometry of [3,3]-Sigmatropic Rearrangements of Iminium IOns, J. of Org. Chem, 53, Feb. 1, 1988, p. 685-690.

Girisuta, et al., "Green Chemicals A Kinetic Study on the Conversion of Glucose to Levulinic Acid," Chemical Engineering Research and Design 84(A5) 339-349 (2006).

Girisuta, et al., "Kinetic Study on the Acid-Catalyzed Hydrolysis of Cellulose to Levulinic Acid," Ind. Eng. Chem. Res. 46: 1696-1708 (2007).

Glansdorp, Freija G., et al., "Synthesis and stability of small molecule probes for *Pseudomonas aeruginosa* quorum sensing modulation", Org. Biomol. Chem., vol. 2, 2004, p. 3330-3336.

Horn, Mihai, et al. "Synthesis and Conformational Analysis of Some 2-Alkyloxycarbonyl Substituted 1,3-Dioxanes", Studia Univ. Babes-Bolyai, Chemia XL, 1-2, 1995, p. 99-108.

Krohn, Karsten and Schafer, Gisbert, "Synthesis of Protected 4-Deoxyaklanonic Acid via Naphthalene-Substituted Oligo ketides", Liebigs Ann. 1996, 265-270.

Nicolaou, K.C., et al., "Asymmetric Total Syntheses of Platensimycin", Angew. Chem. Int. Ed. 2007, 46, 3942-3945.

Sakuda, Shohei, et al., "Biosynthetic Studies on Virginiae Butanolide A, a Butyrolactone Autoregulator from Streptomyces. Part 2.' Preparation of Possible Biosynthetic Intermediates and Conversion Experiments in a Cell-free System", J. Chem. Soc. Perkin Trans., 1993, p. 2309-2315.

Schnebel, Matthias, et al., "Reactions between Benzocyclobutenone Tricarbonylchromium Complexes and Lithium Dialkylphosphides: A New Route to Isochromanones", Eur. J. Org. Chem., 2003, No. 22, 4363-4372.

Anderson, et al., "Preparation of Carboxylic Acids from Protected Aldehydes," J. Org. Chem. 43(17): 3417-3418 (1978).

Babinsky, Ron, "PVC Additives—A Global Review," Journal of Vinyl & Additive Technology 1-4 (2007).

Bayer MaterialScience, "Plasticizers." 23 pages, Mar. 2001.

Bechtold, et al., "Perfectly Alternating Copolymer of Lactic Acid and Ethylene Oxide as a Plasticizing Agent for Polylactide," Macromolecules 34: 8641-8648 (2001).

Boehm, R., "Knowledge on cyclic ketals. Part 11: Synthesis of some new derivatives and separation of their isomers," Pharmazie 36(5): 329-330 (1981).

Brigl, Percy, et al., "The Reaction of the Pyruvic Acid with Glycerin," Annalen der Chemie 476: p. 215-232, Received Oct. 7, 1929, (with English translation).

Briol, et al., "Reaction of pyroracemic acid with glycerol," Ann. 476: 215-232 (1929).

Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).

Carey, et al., "Advanced Organic Chemistry, Second Edition, Part B: Reactions and Synthesis," Plenum Press 539-552 (1983).

Chirila, T., "Pent-and hexatomic cycloacetal esters. Synthesis and characterization of some 2-Carbalkoxymethyl-1,3-dioxolanes (dioxanes)," Revista de Chimie 28: 730-733 (1977).

Cuiling, et al., "Synthesis of Levulinic Ketals with Furfuryl Alcohol as Raw Material," Journal of Huagiao University (Nature Science) 23(3): 257-259 (2002) (English Translation).

Gasparrini, et al., "Synthesis of Dimethyl Acetals, Diethyl Acetals, and Cyclic Acetals Catalyzed by AminoPropylated Silica Gel Hydrochloride," Tetrahedron 40(9): 1491-1500 (1984).

Gelas, et al., "Synthese du 4-oxo et de 4-hydroxy-3,6,8-trioxabicyclo[3.2.1]octanes," Carbohydrate Research 30(1): 21-34 (1973) (with English abstract).

Gonzalez, et al., "Application of Fourier Transform Infrared Spectroscopy in the Study of Interactions Between PVC and Plasticizers: PVC/Plasticizer Compatibility versus Chemical Structure of Plasticizer," Journal of Applied Polymer Science 101: 1731-1737 (2006).

Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).

Haskelbhrg, L., "The preparation of glycerol esters of amino acids," Compt. rend. 190270-190272 (1930).

Hegde, et al., "The Kinetics and Thermodynamics of Bicyclic Ketal Formation: An Application to the Synthesis of the Zaragozic Acids," Tetrahedron 53(32): 11179-11190 (1997).

International Search Report and Written Opinion for PCT/US10/39554 mailed on Aug. 30, 2010, 11 pages.

International Preliminary Report on Patentability for International Application No. PCT/US2009/058365, mailed Apr. 7, 2011.

(56) References Cited

OTHER PUBLICATIONS

Transmittal and International Preliminary Report and Written Opinion on Patentability for PCT/US2010/039554, mailed Dec. 8, 2011, 8 pages.
Krauskopf, Leonard G., "How About Alternatives to Phthalate Plasticizers?," Journal of Vinyl & Additive Technology 9 (4): 159-171 (2003).
Lenz, Robert W., "Structure, Properties, and Cross-linking Reactions of Poly(ester acetals)," Macromolecules 2(2): 129-136 (1969).
Li, et al., "Montmorillonite Clay Catalysis. Part 2. An Efficient and Convenient Procedure for the Preparation of Acetals Catalysed by Montmorillonite K-10," J. Chem Research (S) 26-27 (1997).
Lindblad, et al., "Polymers from Renewable Resources," Advances in Polymer Science 157: 139-161 (2002).
Lukes, Robert M., Preparation of Methyl Esters Containing the 1,3-Dioxane or 2,4,8,10-Tetroxaspiro[5.5]undecane Structure by Ketal Exchange, 26: 2515-2518 (1961).
Meltzer, et al., "2,2-Disubstituted 1,3-Dioxolanes and 2,2-Disubstituted 1,3-Dioxanes," JOC 25: 712-715 (1960).
Meskens, Frans A.J., "Methods for the Preparation of Acetals from Alcohols or Oxiranes and Carbonyl Compounds," Synthesis 501-522 (1981).
Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986).
Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).
Newman, et al.,"Kinetic and Equilibrium Studies of Cyclic Ketal Formation and Hydrolysis," The Journal of the American Oil Chemist's Society 80: 6350-6355 (1958).
Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).
Otera, Junzo, "Esterification, Methods, Reactions, and Applications," Wiley-VCH Verlag GmbH & Co., 1-19 (2003).
Pasto, et al., "Neighboring Group Participation by Carbonyl Oxygen," Journal of the American Chemical Society 87(7): 1515-1521 (1965).
Showler, et al., "Condensation Products of Glycerol with Aldehydes and Ketones. 2-Substituted m-Dioxan-5-OLS and 1,3-dioxolane-4-methanols," Chem. Rev. 67: 427-440 (1967).
Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).
Takenishi, et al., The Syntheses from Levulinic Acid. A Possible Use of Some 2 Methyl-5-oxopyrrolidine-2 carboxylic Esters as Plasticizers, 27(4): 207-209 (1954).
Wang, et al., "An efficient procedure for protection of carbonyls catalyzed by sulfamic acid," Journal of Molecular Catalysis A: Chemical 233: 121-126 (2005).
Yamaguchi, Masahiko, "Synthesis of Polycyclic Aromatic Compounds via Polyketides," Yuki Gosei Kagaku Kyokaishi 45(10) 969-982 (1987) (Chinese-Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Yulan, et al., "Synthesis of Ketals of 4-Oxopentanoates," Lanzhou Daxue Xuebao, Ziran Kexueban 30(2): 66-70 (1994).
Zhang, et al., "Synthesis of Ketals of 4-Oxopentanoates," Lanzhou Daxue Xuebao, Ziran Kexueban 30(2): 66-70 (1994).
Bruice et al., "A Search for Carboxyl-Group Catalysis in Ketal Hydrolysis", J. of Am. Chem. Soc., 89:14, 1967, pp. 3568-3576.
European Search Report for European Application No. 11781170.3, Report Date Dec. 17, 2014, 12 pages.
Gelas, et al., "Organic Chemistry. Dihydroxyl Cyclic Acetals Derived from Glycerol," C.R. Acad. Sc. Paris t. 271: Series C, 218-220 (1970) (English Translation).
Kim, et al., "Transesterification of vegetable oil to biodiesel using heterogeneous base catalyst," Catalysis Today 93-95: 315-320 (2004).
Nakamura, et al., "Study on Ketalization Reaction of Poly(vinyl alcohol) by Ketones. VIII. Kinetic Study on Acetalization and Ketalization Reactions of Poly(vinyl alcohol)," Journal of Polymer Sceince: Part A: Polymer Chemistry 34: 3319-3328 (1996).
Ono, et al., "Synthesis and Properties of Soap Types of Double-Chain Cleavable Surfactants Derived from Pyruvate," J. Oleo Sci. 53(2): 89-95 (2004).
Yang, et al., "Synthesis of acetals and ketals catalyzed by tungstosilicic acid supported on active carbon," Journal of Zhejiang University of Science 6B(5): 373-377 (2005).
Zhang, et al., "Qualitative analysis of products formed during the acid catalyzed liquefaction of bagasse in ethylene glycol," Bioresource Technology 98: 1454-1459 (2007).

* cited by examiner

KETAL COMPOUNDS AND USES THEREOF

CROSS-REFERENCE TO RELATED APPLICATION

This application is a continuation application of U.S. patent application Ser. No. 13/333,273, filed on Dec. 21, 2011, which is a continuation of and claims priority to Patent Cooperation Treaty Application No. PCT/US2010/039554, filed Jun. 22, 2010, which claims the benefit of U.S. Provisional Patent Application No. 61/219,098, filed 22 Jun. 2009, the entire contents of all of the foregoing applications being incorporated herein by reference in their entirety.

DETAILED DESCRIPTION

New chemical compositions based on 1,2- and 1,3-alkanediol, and 1,2- and 1,3-alkanetriol ketals of oxocarboxylate esters are disclosed, as are uses of these compositions as plasticizers for organic polymers and a lubricant.

The 1,2-propanediol ketals of oxocarboxylate esters are known. For example, the 1,2-propanediol ketal of ethyl levulinate is disclosed at http://www.thegoodscentscompany.com/data/rw1597311.html, and the 1,2-propanediol ketal of ethyl acetoacetate is disclosed in U.S. Patent Publication No. 2006/0165622. Other ketals of oxocarboxylates include those based on various 1,2-alkanediols such as ethylene glycol, or those based on 1,3-alkanediols, such as 1,3-propanediol or 1,3-butanediol.

International Patent Publication No. WO 2009/032905 and U.S. Patent Publication No. 2008/0242721 disclose the reaction products of triols, such as glycerol, 1,1,1-trimethylolpropane, or 1,1,1-trimethylolethane, with esters of various oxocarboxylates including alkyl levulinates, alkyl acetoacetates, and alkyl pyruvates. These compounds all feature one free hydroxyl group and one carboxylate ester, acid, or salt per molecule.

A number of known plasticizer compounds are derived from non-renewable, petroleum or natural gas derived feedstocks. Phthalate esters, particularly, dioctyl phthalate ester, di(2-ethylhexyl)phthalate ester, and diisononyl phthalate ester are industrially significant plasticizers useful for plasticizing many formulations; more common formulations include those containing poly(vinyl chloride) (PVC). Recent regulatory pressure has targeted phthalates (United States Environmental Protection Agency Report: Phthalates Action Plan—Dec. 30, 2009) for replacement due to the risks associated with their use. Plasticizer replacements are needed to plasticize formulations without the risk to humans, animals and the environment.

There is a need to provide plasticizers based on non-phthalates, or, more generally, from non-petroleum feedstocks. It is desirable that such materials be synthesized economically in large volumes. A number of lubricating fluids are based on mineral oils that present potential environmental hazards. These formulations have been widely used for many decades. Some demanding lubricant applications include metal working which requires high performance metalworking fluids containing chlorinated paraffins. Recently however, the use of chlorinated paraffins has been questioned due to hazards to workers and the environment. Previous attempts to use non-chlorinated replacements have failed in metalworking requiring high performance lubricating and extreme pressure/anti-wear properties.

There is a need for high performance, economical, environmentally safe lubricating fluids based on renewable biomass feedstocks. It is desirable that such lubricants be readily available, cost-effective, and non-hazardous for delivering key lubricating/anti-wear properties.

SUMMARY

This invention is in one aspect a compound having a structure corresponding to structure I

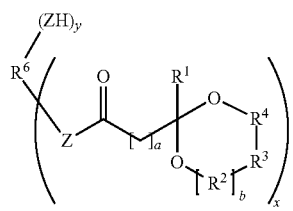

wherein a is from 0 to 12; b is 0 or 1; each $R^1$ is independently hydrogen, a hydrocarbyl group, or a substituted hydrocarbyl group; each $R^2$, $R^3$, and $R^4$ are independently methylene, alkylmethylene, or dialkylmethylene, x is at least 1, y is 0 or a positive number and x+y is at least 2; $R^6$ is a hydrocarbyl group or a substituted hydrocarbyl group and each Z is independently —O—, —NH— or —NR— where R is a hydrocarbyl group or a substituted hydrocarbyl group.

In another aspect, the invention is a mixture comprising at least two different compounds according to structure I.

In another aspect, the invention is a compound having a structure according to structure II

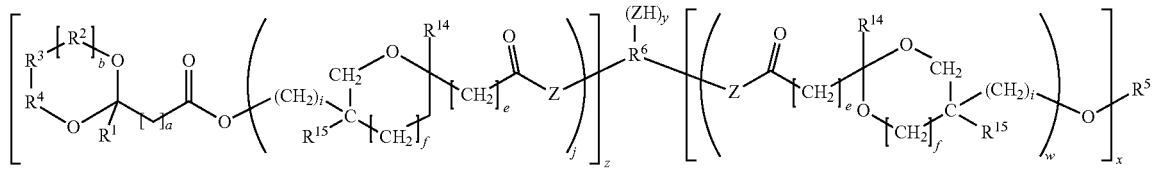

each $R^1$ is independently hydrogen, a hydrocarbyl group, or a substituted hydrocarbyl group; each $R^2$, $R^3$, and $R^4$ are independently methylene, alkylmethylene, or dialkylmethylene; $R^5$ is hydrogen or

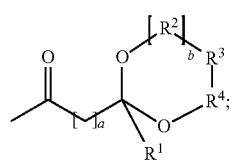

$R^6$ is a hydrocarbyl group or a substituted hydrocarbyl group; each $R^{14}$ and $R^{15}$ are independently hydrogen, a hydrocarbyl, or a substituted hydrocarbyl group; each Z is independently —O—, —NH— or —NR— where R is a hydrocarbyl group or a substituted hydrocarbyl group, each a and each e is independently from 0 to 12; each b and each f is independently 0 or 1; each i is zero or one; each j is zero to 100; w is from 1 to 100; x is at least 1, y is 0 or a positive number and z is zero or a positive number provided that z is at least one when $R^5$ is hydrogen.

In another aspect, the invention is a mixture comprising at least two different compounds according to structure II.

In still another aspect, the invention is a compound having a structure according to structure III

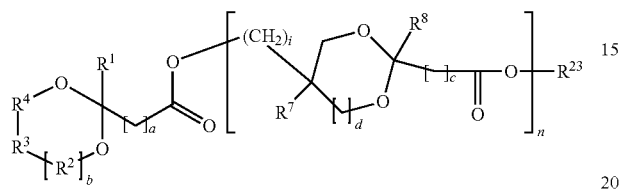

wherein a is from 0 to 12; b is 0 or 1; i is 0 or 1; each $R^1$ is independently hydrogen, a hydrocarbyl group, or a substituted hydrocarbyl group; each $R^2$, $R^3$, and $R^4$ is independently methylene, alkylmethylene, or dialkylmethylene, each $R^7$ and each $R^8$ are independently hydrogen, a hydrocarbyl, or a substituted hydrocarbyl group; each $R^{23}$ is a hydrocarbyl group or substituted hydrocarbyl group having between 1 and 12 carbon atoms; c is from 0 to 12; d is 0 or 1; and n is a number from 1 to 100.

In another aspect, the invention is a mixture comprising at least two different compounds according to structure III.

In another aspect, the invention is a compound having a structure corresponding to IV

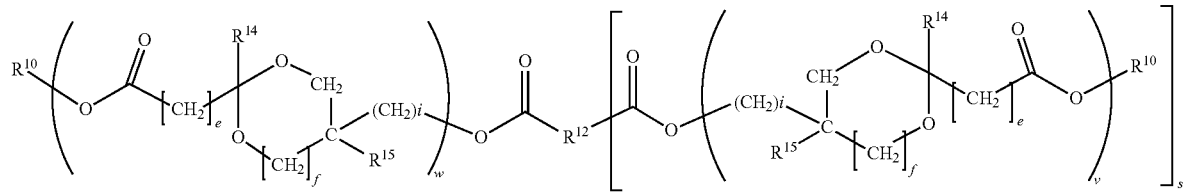

wherein each e is independently from 0 to 12; each f is independently 0 or 1; each i is independently 0 or 1; each $R^{10}$ is independently a hydrocarbyl group or a substituted hydrocarbyl group; each $R^{14}$ and each $R^{15}$ are independently hydrogen, a hydrocarbyl, or a substituted hydrocarbyl group; $R^{12}$ is a covalent bond, a hydrocarbyl group or a substituted hydrocarbyl group; w is a number from 1 to 100, v is a number from 0 to 100 and s is at least one.

In another aspect, the invention is a mixture comprising at least two compounds of structure IV.

In still another aspect, the invention is mixture of two or more compounds selected from compounds of structure I, compounds of structure II, compounds of structure III and compounds of structure IV.

The invention in other aspects is a composite comprising a compound of structure I, structure II or structure III or structure IV, or any combination of two or more thereof, and a polymer.

The invention is also a process for plasticizing a polymer comprising melt or solution blending a polymer and a plasticizing amount of at least one compound of structure I, at least one compound of structure II, at least compound of structure III, at least one compound of structure IV or a mixture of two or more of compounds having structures I, II, III IV or V.

In yet another aspect, the invention is a method for making an ester or amide compound according to structure I comprising:

a. contacting reagents comprising (A) one or more alkylketal esters having the structure

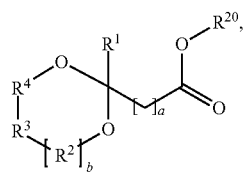

(B) a catalyst and (C) a polyol having the structure $R^6(OH)_t$ or a polyamine having the structure $R^6(NRH)_t$ or $R^6(NH_2)_t$ where R is a hydrocarbyl or substituted hydrocarbyl group and b. effecting a reaction to form an alcohol and a compound of claim 1, wherein $R^1$, $R^2$, $R^3$, $R^4$, $R^6$, Z, a, b, x, y and z are as defined above, t=x+y and $R^{20}$ is a hydrocarbyl group or substituted hydrocarbyl group having up to 36 carbon atoms.

The invention is also making an ester compound of structure II comprising:

a. contacting reagents comprising (1) one or more alkylketal esters having the structure

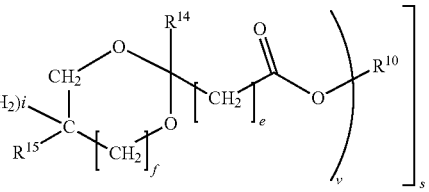

(2) one or more hydroxyalkyl ketal esters having the structure

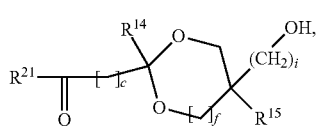

(3) a catalyst and (4) a polyol having the structure $R^6(OH)_t$ or a polyamine having the structure $R^6(NRH)_t$ or $R^6(NH_2)_t$ where R is a hydrocarbyl or substituted hydrocarbyl group; and b. effecting a reaction to form an alcohol and a compound of structure II, wherein $R^1$, $R^2$, $R^3$, $R^4$, $R^6$, $R^{14}$, $R^{15}$, Z, a, b, e, f, i, j, w, x, y, z and n are as defined above, t=x+y+z, $R^{20}$ and $R^{21}$ are each independently a hydrocarbyl group or substituted hydrocarbyl group having up to 12 carbon atoms and $R^5$ is hydrogen or

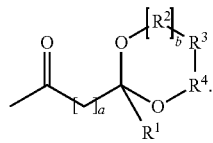

The invention is in another aspect a method for making an ester compound of structure III comprising:
a. contacting reagents comprising (1) one or more alkylketal ester having the structure

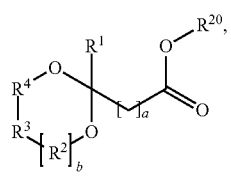

(2) one or more hydroxyalkyl ketal esters having the structure

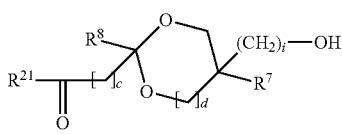

and (3) a catalyst; and
b. effecting a reaction to form an alcohol and a compound of structure III, wherein $R^1$, $R^2$, $R^3$, $R^4$, $R^7$, $R^8$, $R^{23}$, a, b, c, d and n are as defined above, and $R^{20}$ and $R^{21}$ are each independently a hydrocarbyl group or substituted hydrocarbyl group having up to 12 carbon atoms.

The invention is in still another aspect a method of making an ester comprising contacting reagents comprising (1) one or more hydroxyalkyl ketal esters having the structure

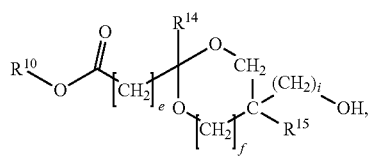

(2) a full or partial ester of a polycarboxylic acid, and (3) a catalyst; and effecting a reaction to form the ester compound and an alcohol, wherein e is from 0 to 12; f is 0 or 1, i is zero or 1, each $R^{10}$ is independently a hydrocarbyl group or a substituted hydrocarbyl group; each $R^{14}$ and each $R^{15}$ are independently hydrogen, a hydrocarbyl, or a substituted hydrocarbyl group.

In another aspect, the invention is a method of making a compound of structure I comprising:
a. reacting a compound comprising a structure corresponding to

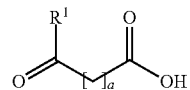

with a polyol comprising a structure corresponding to $R^6(OH)_t$ in the presence of a catalyst to form water and a compound comprising a structure corresponding to

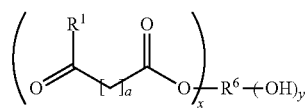

b. adding a compound comprising a structure corresponding to

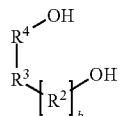

and c. effecting a reaction to form water and a compound having a structure corresponding to claim 1, wherein a, b, $R^1$, $R^2$, $R^3$, $R^4$ and $R^6$ are as defined in claim 1, x is at least 1, y is zero or a positive number and t=x+y.

The invention is also a lubricant composition comprising an antioxidant and a compound having structure I, II, III, IV or a mixture of two or more such compounds. The invention is also a method for lubricating at least two contacting surfaces, the method comprising introducing the lubricant composition between the two contacting surfaces.

The structure I products correspond to a reaction product of a polyol, aminoalcohol or polyamine and certain 1,2- and/or 1,3-alkanediol ketal of an oxocarboxylate esters, although the invention is not limited to any particular preparation method. 1,2- and 1,3-alkanediols ketals of oxocarboxylate esters are sometimes referred to herein as "alkylketal esters". Up to one mole of alkyl ketal ester can be reacted per equivalent of hydroxyl groups or amino groups provided by the polyol, aminoalcohol or polyamine. The polyol, aminoalcohol or polyamine is most preferably difunctional, but polyols, aminoalcohols and polyamines having more than two hydroxyl and/or amino groups can be used.

The values of x and y in structure I will depend on the number of hydroxyl groups or amino groups on the polyol, aminoalcohol or polyamine, the number of moles of the alkyl ketal ester per mole of the polyol, aminoalcohol or polyamine, and the extent to which the reaction is taken towards completion. Higher amounts of the alkyl ketal ester favor lower values for y and higher values of x.

In structure I, y is preferably from 0 to 2 and x is preferably at least 2. All a in structure I are preferably 2, and all $R^1$ are preferably methyl. In some embodiments of structure I, all Z are —O—, y is 0 and x is 2; these products correspond to a reaction of two moles of an alkyl ketal ester and one mole of a diol. In some other embodiments, all Z are —O—, y is 1 and x is 1; these products correspond to the reaction of one mole of the alkyl ketal ester and one mole of a diol.

When Z is —O—, $R^6$ corresponds to the residue, after removal of hydroxyl groups, of a polyol having the structure $R^6(OH)_t$, where t=x+y. No two hydroxyl groups should be bonded to the same carbon atom. Suitable polyols include alkane diols such as ethane diol, 1,2-propane diol, 1,3-propane diol, 1,4-butane diol, 1,5-pentane diol and 1,6-hexane diol, 1,4-cyclohexanediol, glycerine, trimethylolpropane, trimethylolethane, pentaerythritol, erythritol, sucrose, isosorbide, sorbitol, bisphenol-A, 2,3-dibromobutene-1,4-diol, 1,4-benzene dimethanol, 1,4-benzenediol (hydroquinone), 2-butyne-1,4-diol, 3-hexyne,3,5-diol and other alkyne-containing polyols such as those marked under the Surfynol™ brand name by Air Products and Chemicals. Other suitable polyols contain ether groups; these include glycol ethers such as diethylene glycol, triethylene glycol, dipropylene glycol, tripropylene glycol. Other suitable ether-containing polyols include hydroxyl-terminated polyethers such as poly(ethylene oxide), polypropylene oxide), ethylene oxide-propylene oxide copolymers and polymers of tetramethylene glycol; these may have molecular weights of up to 6000, preferably up to 1000 and more preferably up to 150. The polyol may contain ester linkages; these polyols include those formed by condensation or step-growth polymerization of diols and dicarboxylic acids (or their derivatives), including a polyester of diethylene glycol and phthalic acid or phthalic anhydride. The $R^6$ group preferably contains from 2 to 24, especially from 2 to 12 or from 2 to 6 carbon atoms.

When all Z are —NR— or —NH—, $R^6$ corresponds to the residue, after removal of amino groups, of a polyamine having the structure $R^6(NRH)_t$ or $R^6(NH2)_t$ where t=x+y. No two amino groups should be bonded to the same carbon atom. Examples of suitable polyamines include hydrazine, ethane-1,2-diamine, 1,6-hexanediamine, but-2-ene-1,4-diamine, Metformin, butane-1,4-diamine, propane-1,2-diamine, piperazine, 2,2,4-trimethyl-1,6-hexanediamine, 2,4,4-trimethyl-1,6-hexanediamine, benzene-1,3-diamine, 2-methylbenzene-1,3-diamine, 4-chlorobenzene-1,3-diamine, and polyoxyalkyleneamines having two amine groups, such as those sold under the trade name JEFFAMINE®, (Huntsman Corp.; Salt Lake City, Utah), diamines such as those sold under the trade name ELASTAMINE® (Huntsman Corporation), phenylene diamine, methylene bis(aniline), diethyltoluenediamine and the like.

When the Z groups in structure I include at least one —O— and at least one —NH— or —NR-linkage, $R^6$ corresponds to the residue, after removal of hydroxyl and primary or secondary amino groups, of an aminoalcohol, where the combined number of hydroxyl, primary and secondary amino groups is equal to x+y. Examples of suitable aminoalcohols include 2-aminoethanol, 3-aminopropan-1-ol, isopropanolamine, 2-aminopropan-1-ol, 2-aminobutan-1-ol, 2-amino-3-methylbutan-1-ol, 2-amino-4-methylpentan-1-ol, 6-aminohexan-1-ol, 1-amino-3-chloropropan-2-ol, 7-aminobicyclo[2.2.2]octan-8-ol, 2-aminopyridin-3-ol, 2-amino-4-phenylphenol, 5-aminonaphthalen-1-ol, and 4-(4-aminophenyl)phenol.

In structures I-IV herein, a "substituted" hydrocarbon or hydrocarbyl group may contain any substituents that do not react with carboxylate groups, hydroxyl groups or amino groups under the conditions of the reactions that form the various products of structures I-IV. Therefore, the substituents should exclude groups such as hydroxyl, primary or secondary amino, mercapto, carboxylic acid or salts or esters thereof, carboxylic acid halides, sulfur- or phosphorus-containing acids, isocyanates and the like. In addition, the substituent groups also should not otherwise interfere with the reactions that form the various products of structures I-IV. Suitable substituents include carbonyl, halogen, tertiary amino, ether, sulfone, and the like, among others.

Some specific compounds according to structure I include those having the structure

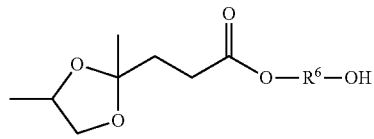

or the structure

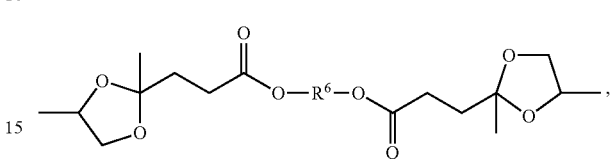

particularly in which $R^6$ is —$(CH_2)$—$_m$ wherein m is from 2 to 18, especially 2, 3, 4 or 6.

Compounds according to structure I can be prepared in a transesterification or ester-aminolysis reaction between the corresponding polyol, aminoalcohol or polyamine and the corresponding alkyl ketal ester. Alternatively, compounds according to structure I can be prepared by reacting an oxocarboxylic acid with the polyol, aminoalcohol or polyamine to form an ester or amide, and then ketalizing the resulting product with a 1,2- or 1,3-alkane diol such as ethylene glycol, 1,2-propanediol, 1,3-propanediol, 1,2-butanediol, 1,3-butanediol, 1,2-pentanediol, 1,3-pentanediol, 1,2-hexanediol, 1,3-hexanediol, and the like. Ketalization is conveniently performed according to the methods described in International Patent Publication No. WO 2009/048874, or U.S. Patent Publication No. 2008/0242721.

A mixture of products is commonly obtained from the synthesis process. For example, it is common for the reaction product to contain a mixture of materials having various values of x and y. It is preferred that no more than 25 mole percent of the product represents compounds in which y is 1 or greater. In especially preferred cases in which the starting polyol is a diol, it is preferred that at least 75 mole of the product is species in which x is 2 and y is zero.

Compounds corresponding to structure II correspond to the reaction product of a polyol of the structure $R^6(OH)_t$, an amino alcohol or a polyamine having the structure $R^6(NRH)_t$ or $R^6(NH_2)_t$, in which t=x+y+z, one or more alkyl ketal esters having the structure

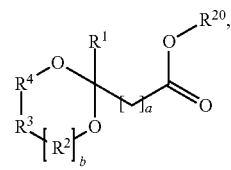

and one or more triol ketals of an oxocarboxylate ester having the structure

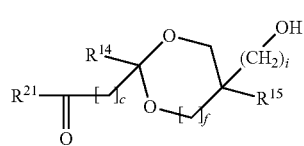

wherein the variables are as defined before. $R^6$ is as described above with respect to structure I. Ketals of triols with oxocarboxylate esters are sometimes referred to herein as "hydroxyalkyl ketal esters". Some examples of useful alkylketal ester starting materials include the 1,2-propane diol ketal of ethyl levulinate, the 1,3-propane diol ketal of propyl levulinate, 1,2-propane diol ketal of butyl levulinate, 1,3-propane diol ketal of ethyl levulinate and 1,2-ethane diol ketal of ethyl levulinate. Some examples of useful hydroxyalkyl ketal ester starting materials include the 1,2-glycerol ketal of methyl levulinate, 1,2-glycerol ketal of ethyl levulinate, 1,2-glycerol ketal of methyl acetoacetate, and 1,2-glycerol ketal of ethyl acetoacetate. Useful methods for making such alkyl ketal esters and hydroxyalkyl ketal esters are described in U.S. Patent Publication No. 2008/0242721 and International Patent Publication No. WO 2009/048874, which are incorporated herein by reference in their entirety.

The values of j, w, x, y and z in structure II will depend on factors including the number of hydroxyl or amino groups on the polyol, aminoalcohol or polyamine, the number of moles of alkyl ketal ester per mole of the polyol, aminoalcohol or polyamine, the number of moles of the hydroxyalkyl ketal ester per mole of the polyol, aminoalcohol or polyamine, and the extent to which the reaction is taken towards completion. Higher amounts of the alkyl ketal ester favor lower values for y. Higher amounts of the hydroxyalkyl ketal ester favor lower values of y, and higher values of x and z and/or higher values of j and w.

When j or w is greater than 1 in structure II, some amount of self-condensation ("oligomerization") of the hydroxyalkyl ketal ester has taken place.

In some embodiments of the structure II compound, $R^5$ is

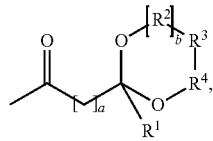

and (a) j=0, z is at least one and w is from 1 to 15, (b) z=0, x=1 and w is from 1 to 15 or (c) z=0, x is greater than 1 and w is from 1 to 15. In some other embodiments of the structure II compound, $R^5$ is hydrogen, j is from 0 to 15, and z is at least one. In some embodiments of the structure II compound, including those specific embodiments just mentioned, each Z is —O—.

In structure II, including the specific embodiments mentioned in the preceding paragraph, a and all e preferably are 2, all $R^1$ and $R^8$ preferably are methyl and $R^{14}$ is preferably an alkyl group, especially one having up to 4 carbon atoms. $R^6$ in any of the foregoing embodiments may include ether or ester groups.

Compounds according to structure II can be prepared in a transesterification reaction between the corresponding polyol, aminoalcohol or polyamine, the corresponding alkyl ketal ester and the corresponding hydroxyalkyl ketal ester. In some embodiments, all three of these materials are combined and reacted in a single step to form the structure II material. In other embodiments, the compound is formed in a one-pot process in which the reagents are added sequentially; in such a case the hydroxyalkyl ketal ester may be starve-fed to the reaction to minimize oligomerization.

In other embodiments, the polyol, aminoalcohol or polyamine and hydroxyalkyl ketal ester are reacted first to form an intermediate, which is then reacted with the alkyl ketal ester. In still other embodiments, when the value of j and/or w in structure II is greater than 1, the hydroxyalkyl ketal ester can be oligomerized in a preliminary step, and the oligomerized material is then reacted with the other starting materials or with an intermediate formed by reaction of the polyol, aminoalcohol and/or polyamine and the alkyl ketal ester. Oligomerization of the hydroxyalkyl ketal ester also can be performed at the same time that the hydroxyalkyl ketal ester reacts with the other starting materials.

Again, a mixture of products is commonly obtained from the synthesis process. For example, it is common for the reaction product to contain a mixture of materials having various values of j, w, x, y and z.

The structure III compounds correspond to certain reaction product of an alkyl ketal ester having the structure

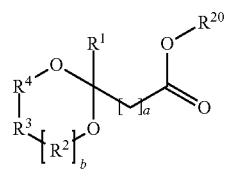

wherein the variables are as defined before, and a hydroxyalkyl ketal ester having the structure

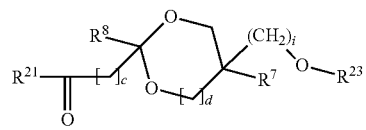

where again the variables are as defined before. Suitable alkyl ketal esters include those described above with respect to structure I. Suitable hydroxyalkyl ketal esters include those described above with respect to structure II.

In structure III, n is preferably from 1 to 15, a and all c are preferably 2, $R^1$ and $R^8$ are preferably methyl and $R^{23}$ is preferably an alkyl or phenyl group. As with structure II, a value of n greater than 1 indicates that some oligomerization of the hydroxyalkyl ketal ester has occurred, n is more preferably from 1 to 2 and may be 1. The structure III compound is a 1:1 reaction product of the starting materials when n is 1. An example of a compound according to structure III is

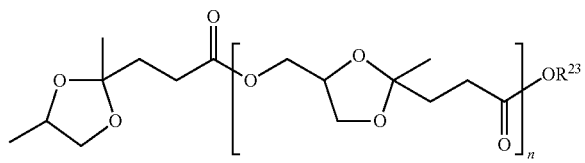

wherein $R^{23}$ is as defined above.

Compounds according to structure III can be prepared in a transesterification reaction between the corresponding alkyl ketal ester and the corresponding hydroxyalkyl ketal ester. The values of n in structure III will depend on the relative number of moles of the alkyl ketal ester and hydroxyalkyl ketal ester, and the extent to which the reaction is continued. Higher amounts of the hydroxyalkyl ketal ester favor higher values of n. When n is greater than 1, indicating that the hydroxyalkyl ketal ester has oligomerized, it is possible to perform the oligomerization reaction separately, in a preliminary step. Alternatively, the oligomerization can be performed at the same time as the reaction with the alkyl ketal ester. If oligomerization is to be minimized or prevented, the hydroxyalkyl ketal ester may be starve-fed to the alkyl ketal ester under reaction conditions.

Compounds according to structure IV correspond to reaction products of transesterification reaction between a full or partial polycarboxylic acid ester compound and one or more hydroxyalkyl ketal esters as described above.

The full or partial polycarboxylic acid ester compound is a material that contains more than one carboxyl group per molecule, at least one of which is esterified, preferably with a hydrocarbyl or substituted hydrocarbyl group having up to 12 carbon atoms, especially up to 6 carbon atoms. If all of the carboxyl groups are esterified, the polycarboxylic ester compound is said to be a full ester. A partial ester is one in which only a portion of the carboxyl groups are esterified; the remaining carboxyl groups may be in the acid or salt form. In some embodiments, the polycarboxylic acid ester may contain from 2 to 8 carboxylic acid or carboxylic acid groups, but preferably it contains from 2 to 4 such groups and more preferably is a monoester or a diester of a dicarboxylic acid.

The full or partial ester can be represented by the structure $R^{12}$—$(COOX)_n$, where $R^{12}$ is as defined before, n=1+s, and X is hydrocarbyl or substituted, hydrogen or a monovalent cation, further provided that at least one X is hydrocarbyl or substituted hydrocarbyl. It is preferred that all X are hydrocarbyl or substituted hydrocarbyl.

Examples of full or partial polycarboxylic acid esters suitable for forming the reaction product corresponding to IV include monoesters and diesters of dicarboxylic acids in which $R^{12}$ is a covalent bond, divalent alkyl (especially those of the form —$(CH_2)_k$— where k is from 1 to 20, especially 2 to 10), divalent alkenyl (especially the cis or trans form of —CH=CH—), divalent alkynyl, phenylene, substituted phenylene, and the like. Examples of suitable full or partial carboxylic acid esters include various esters of oxalic, malonic, adipic, sebacic, azealic, maleic, fumaric, butandoic, succinic, dodecanoic and octadecandioic acids. In some embodiments, suitable diesters include diethyl adipate, diethyl sebacate, diethyl succinate, dimethyl adipate, dibutyl adipate, dioctyl adipate, dioctyl-phthalate, and butyl-benzyl phthalate.

Suitable hydroxyalkyl esters include those described above with respect to structure II.

In structure IV, the values of w, s and v will depend on factors including the number of carboxylic acid or carboxylic acid ester groups on the full or partial carboxylic acid ester, the number of moles of hydroxyalkyl ketal ester per mole of the full or partial carboxylic acid ester, and the extent to which the reaction is taken towards completion. Higher amounts of the hydroxyalkyl ketal ester favor higher values of w, s and v. s is preferably from 1 to 7, more preferably from 1 to 3 and most preferably 1. w and v may each be from 1 to 100, preferably from 1 to 10. In some embodiments, w and v are each 1. In other embodiments, w+v is at least 3. In still other embodiments, v=0. When w=1, v=0 and s=1, the product corresponds to a 1:1 reaction product of the hydroxyalkyl ketal ester and a dicarboxylic acid mono- or diester. When w=v=s=1, the product corresponds to a 2:1 reaction product of the hydroxyalkyl ketal ester and a dicarboxylic acid mono- or diester. When either or both of w and v are greater than 1, the molecular weight of the structure IV material may range from about 200 to 40,000 daltons, but is preferably from 300 to 3000 daltons.

In structure IV, the value of each e is preferably 1 or 2, each $R^{14}$ is preferably methyl and each $R^{15}$ is preferably alkyl having up to 3 carbon atoms. Each $R^{10}$ is preferably $C_{1-8}$ alkyl, more preferably $C_{2-4}$ alkyl.

Specific examples of useful compounds of structure IV include,

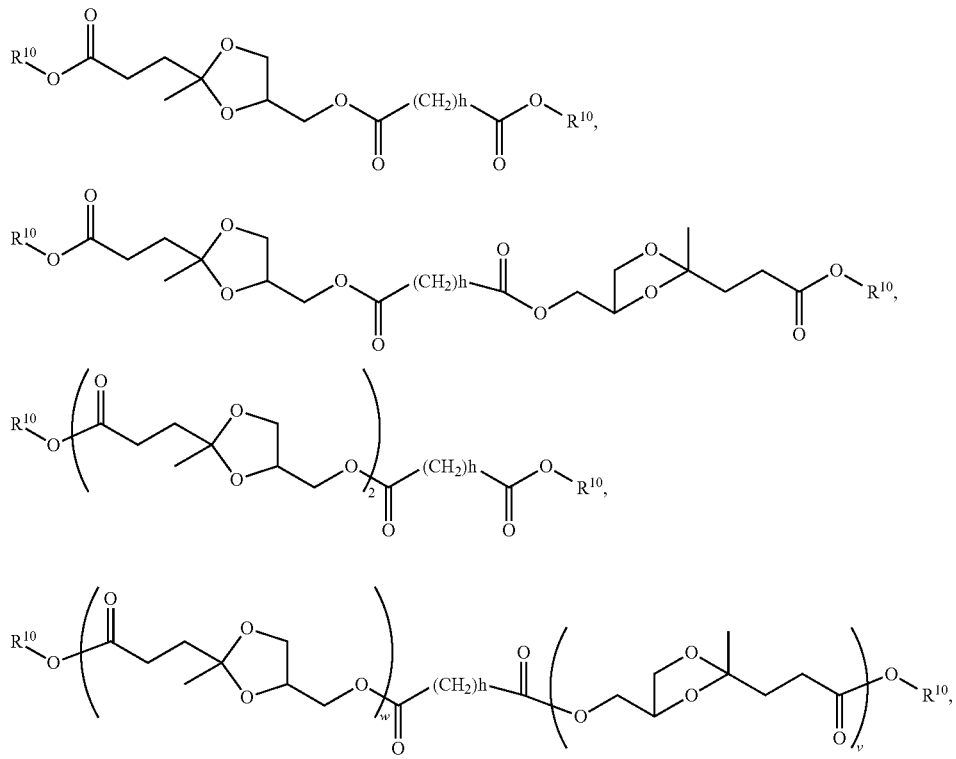

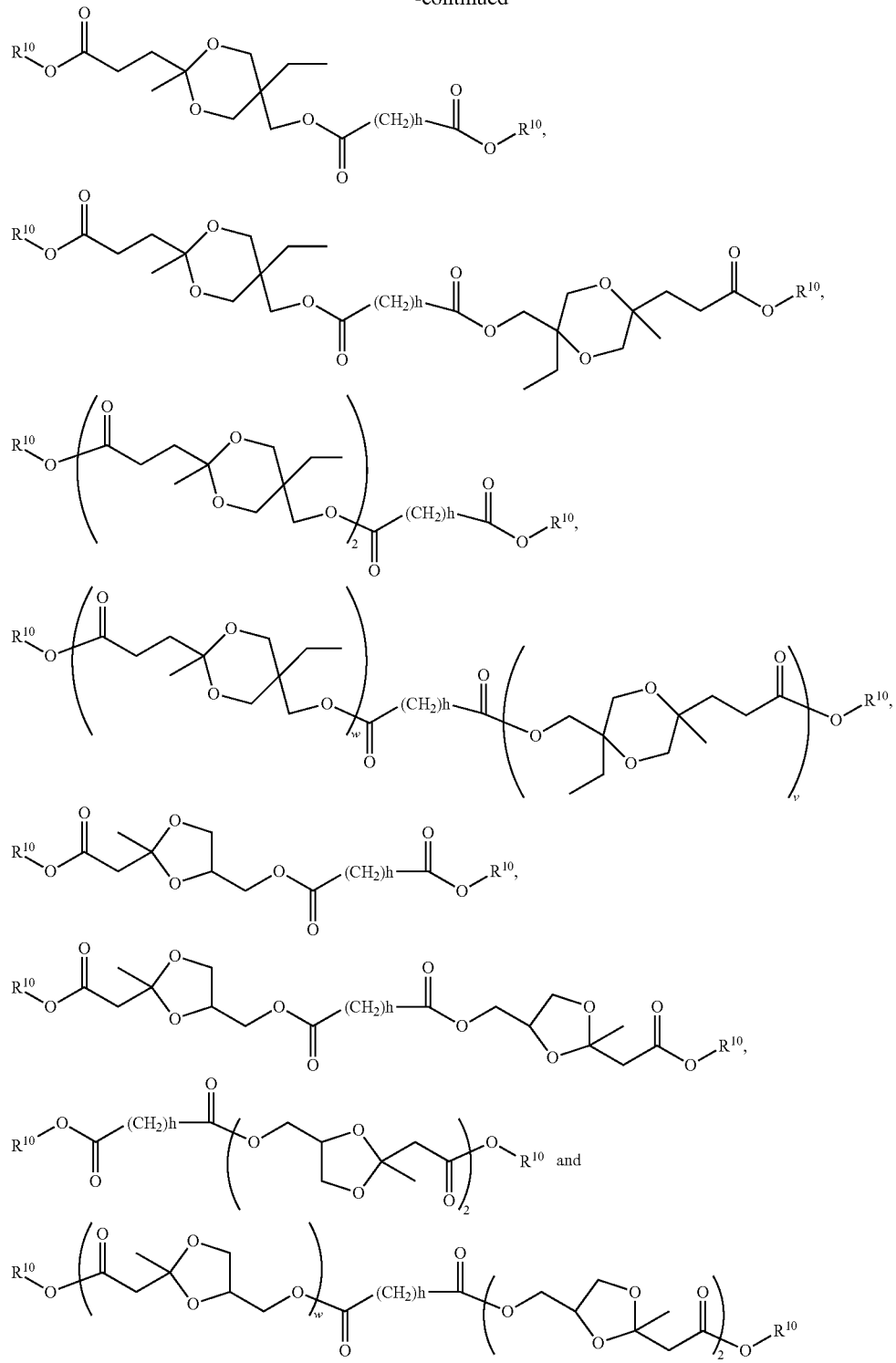

wherein h=0 to 34, preferably 2, 3, 4 or 6 and each $R^{10}$ is independently $C_1$-$C_{12}$ alkyl, preferably $C_1$-$C_4$ alkyl, or aromatic or alkyl aromatic of up to 12 carbon atoms.

Compounds according to structure IV can be prepared in a transesterification reaction between the corresponding full or partial polycarboxylic acid ester and the corresponding hydroxyalkyl ketal ester. In some embodiments, the materials are combined and reacted in a single step to form the structure IV material. In other embodiments, when the value of n in structure IV is greater than 1, the hydroxyalkyl ketal ester can be oligomerized in a preliminary step, and the oligomerized material is then reacted with the full or partial polycarboxylic acid ester. Oligomerization of the hydroxyalkyl ketal ester also can be performed at the same time that material reacts with the full or partial polycarboxylic acid ester. As before, oligomerization of the hydroxyalkyl ketal ester can be minimized or prevented by starve-feeding the material into the reaction under reaction conditions.

In some embodiments, a stoichiometric excess of hydroxyalkyl ketal ester is employed with respect to the full or partial polycarboxylic acid ester in order to form a reaction product having structure IV. In some cases, about two equivalents of hydroxyalkyl ketal ester are employed per mole of carboxylate ester in one or more transesterification reactions. In other embodiments, greater than about 2 and up to 100 equivalents of hydroxyalkyl ketal ester are employed per equivalent of the polycarboxylic acid ester in the reaction to form compound IV. This mole ratio may be between about 2.1 to 50:1 or about 2.2-5:1. In still other embodiments, less than a 2:1 molar ratio of hydroxyalkyl ketal ester to full or partial polycarboxylic acid ester is used, although higher ratios can be used if the reaction is not taken to full conversion. In some other embodiments, where a 1:1 reaction product of the hydroxyalkyl ketal ester and the full or partial polycarboxylic acid ester is desired, about 1 to 10 equivalents of polycarboxylic acid ester is employed per mole of hydroxyalkyl ketal ester.

As before, a mixture of products is commonly obtained from the synthesis process. For example, it is common for the reaction product to contain a mixture of materials having various values of w, v, and s. In some embodiments, a mixture of products is obtained, which includes species in which w and s are 1 and v is zero, as well as species in which w, s and v are all 1. In some embodiments, at least 75 wt. %, more preferably at least 85 wt. %, of such a mixture is the species in which w, s, and v are all 1. In other embodiments, such a mixture contains no more than 10 wt. % or no more than 5 wt. % of the mixture is the species in which w, s and v are all 1.

Certain compounds according to structures I-IV may exist as optical and/or geometrical isomers. In such cases, any of the isomers are suitable.

The transesterification reactions that are used to form the compounds of structures I-IV can be carried out in the presence of an inert solvent, such as hexane, toluene, dichlorobenzene and the like. In other embodiments the reaction is carried out neat. In some embodiments, the reaction is performed at temperature and pressure conditions such that the condensation coproduct, i.e., an alcohol in most cases but water in some cases, evaporates from the reaction mixture, wherein the vapor is condensed and thereby removed. In some embodiments, a temperature between about 60° C. and 300° C. is employed; in other embodiments, a temperature of about 100° C. to 250° C. is employed; in still other embodiments, a temperature of about 160° C. to 240° C. is employed to accomplish the reaction. In some embodiments, pressure in the reaction vessel is lowered to below atmospheric pressure to assist in the removal of the condensation by-product, i.e., the alcohol or water. In some embodiments, nitrogen is sparged or swept through the reaction mixture to assist in the removal of the coproduct alcohol.

The various reactions described above are typically performed in the presence of a catalyst. While the choice of catalyst employed in the reactions is not particularly limited within the scope of the disclosure, a preferred set of embodiments employs metallic catalysts, for example, a catalyst based on titanium, aluminum, zirconium, or tin, such as titanium tetraisopropoxide (Ti(OiPrM), or tin (II) octanoate, or organic zirconates. Other suitable catalysts are, for example, organic titanates and zirconates marketed under Tyzor® brand by DuPont deNemours and Co. of Wilmington, Del. In some embodiments, more than one species of catalyst is used; thus, blends of one or more catalysts such as those mentioned above may be used in a mixture to catalyze the formation of compounds of structures I-IV.

In some embodiments, catalysts such as inorganic bases, including sodium methoxide, sodium ethoxide, calcium acetate, and potassium methoxide, can be used. Organo-ammonium and organo-phosphonium catalysts can be used, such as tetramethylammonium hydroxide, tetrabutyl phosphonium hydroxides and acetates Strong acid catalysts, including camphorsulfonic acid or sulfuric acid can be used in ketalization and esterification reactions. Catalysts are used in amounts suitable to catalyze the reaction. In embodiments, the amount of organometallic catalyst employed is about 5 to 50,000 ppm based on the weight of the total weight of reagents, or about 10 to 500 ppm based on the total weight of reagents.

In some embodiments, the catalyst is incorporated into, or onto, or covalently bound to, a solid support material. Resin beads, membranes, porous carbon particles, zeolite materials, and other solid support materials may be functionalized with catalytic moieties that are, in embodiments, covalently bound or strongly sorbed to one or more surfaces of the solid support.

In some embodiments, it is desirable to deactivate the catalyst after the reaction is complete. Deactivation is useful in embodiments, for example, where distillation or a high temperature process or application is to be employed. Deactivation is accomplished by any convenient technique; the method is not particularly limited by the method of deactivation. Examples of deactivating materials include phosphite compounds such as water, and phenol based compounds such as IRGAFOS® 168 and PEP-Q®, or IRGANOX® MD 1024 (BASF®; Ludwigshafen am Rhein, Germany), and carboxylic acids such as salicylic acid and the like.

The various synthesis reactions described herein can be carried out batch wise or in continuous mode, depending on equipment, scale, and other reaction parameters. The reaction vessel may be made of any suitable material. In some embodiments, the reagents are dried before addition of catalyst, using any convenient technique. In embodiments, drying is accomplished by warming the reaction vessel to about 60° C.-110° C. and applying a vacuum of 5-20 Torr for at least about an hour; in other embodiments a dry inert gas, such as nitrogen or argon, is swept continuously through the vessel instead of applying a vacuum. The reagents are, in some embodiments, analyzed for water content prior to addition of catalyst to the vessel. In other embodiments, the reagents are dried separately prior to addition to the reaction vessel and are introduced to the vessel by a closed system, such as by pipes or tubes, which does not entrain water or air during introduction of the reagents to the vessel.

The catalyst may be added batchwise or in continuous fashion to the vessel. In embodiments, during the addition of catalyst, the reagents are at the same temperature as employed during drying. In other embodiments the reagents are preheated to a targeted temperature, for example in the ranges specified above, prior to addition of the catalyst. After catalyst addition, in some embodiments, a vacuum is employed to remove any air that has become entrained during the addition. In other embodiments, the catalyst is introduced to the vessel by a closed system, such as by pipes or tubes that do not entrain water or air during introduction of the reagents to the vessel. The reaction is, in embodiments, carried out under an inert gas blanket or an inert gas sparge, and agitated using any convenient means of agitation.

In embodiments, the reaction is complete in less than about 2 hour; in other embodiments the reaction is complete between about 1 hour and 12 hours; in still other embodiments the reaction is complete in about 2 to 8 hours. In some embodiments, the limiting reagent in the reaction is metered in gradually by employing an addition funnel, metered pump, or another apparatus known in the industry. Metering of a reagent is, in embodiments, initiated after or during addition of the catalyst and is particularly useful where the reaction is accomplished in a continuous process.

If desired, the crude reaction product can be purified using any convenient techniques, one of which is distillation. A distillation may be performed under reduced pressure or with the aid of nitrogen sparging. It is preferred to perform the distillation in a way that minimizes heat history. Therefore, this step is preferably performed below temperatures at which degradation, color formation, or another side reaction occurs, or if such temperatures are used, the distillation should be performed to minimize the exposure time of the product to such temperatures. In some embodiments, it is desirable to maintain temperatures at or below 200° C. during purification. In other embodiments, it is desirable to maintain temperatures at or below 175° C. during purification. Techniques such as wiped film evaporation, falling film evaporation, and membrane pervaporization are useful. Purification is carried out either with or without prior deactivation of the catalyst.

In some cases, in which mixtures of reaction products are obtained, it may be desirable to separate one or more of those reaction products from the mixture of reaction products, in order to obtain a product that is enriched in (or even consists of) a specific compound or mixture of compound. This can be performed by any suitable technique, including distillation, solvent extraction, chromatographic methods, and the like.

Compounds according to structures I-IV are useful components in compositions that also contain an organic polymer. A very wide range of organic polymers is useful, depending of course on particular applications. The organic polymer may be thermoset or thermoplastic.

Many compounds according to structure I-VI have Hildebrand Solubility Parameters ("HSP") of at least 12 (MPa)$^{1/2}$, quite typically from 12 to 20 MPa)$^{1/2}$. Such compounds tend to be quite compatible with organic polymers having Hildebrand
Solubility Parameters ("HSP") of about 16 (MPa)$^{1/2}$ or greater, therefore preferred compositions are those in which the organic polymer has a Hildebrand Solubility Parameters ("HSP") of about 16 (MPa)$^{1/2}$ or greater. The good compatibility of these tends to make the compound of structure I-IV difficult to extract from the composition, and also makes the composition less likely to exude or leach the plasticizer material.

Extractability in various extractants such as hexanes, soapy water, and mineral oil can be evaluated according to the ASTM D 1239 procedure; weight losses on this test are preferably no greater than 2% and still more preferably no greater than 1% for preferred compositions of the invention. Migration of a plasticizer from an article causes increased exposure of the plasticizer to the environment. The increased exposure can cause adhesive failure, cracking of materials in contact with the article, and contamination of fluids in contact with the article. Additionally, migration out of the articles can lead to stiffening, loss of performance and increase in $T_g$.

Some examples of suitable organic polymers include poly (vinyl chloride), poly(vinylidene chloride), polyhydroxyalkanoates, poly(lactic acid), polystyrene, polycarbonates, polyurethanes or ureas, acrylic polymers, styrene-acrylic polymer, vinyl-acrylic polymers, ethylene-vinyl acetate polymers, polyesters, polyamides, polyethers, acrylonitrile-butadiene-styrene polymers, styrene-butadiene-styrene polymers, polyvinyl acetate, poly(vinyl butyrate), polyketal esters and copolymer thereof, cellulosics, thermoplastic elastomers, or random, graft, or block copolymers thereof or mixtures thereof.

Compounds according to structures I-IV are generally renewable bio-based feedstocks, wherein "bio-based" is used as defined in ASTM D6866. As such, these compounds offer opportunities to replace petroleum-based products such as plasticizer with bio-based materials. Such a bio-based compound can be blended with a bio-based organic polymer to form a polymer composition which is also bio-based. One such polymer is poly(lactic acid), or PLA. Compounds according to any of structures I-IV are good plasticizers for PLA. Compounds I-IV often have high permanence in PLA compared to other compatible plasticizers. The compound according to structures I-IV may be incorporated into an organic polymer composition using any suitable technique such as mechanical blending or compounding, melt blending, solution blending and the like. When the organic polymer is a thermoset, the compound may be blended into one or more precursor materials, which are subsequently cured or otherwise polymerized to form the thermosetting polymer.

A composition containing a compound according to any of structures I-IV and an organic polymer may take the form of a homogeneous blend, a dispersion of one component into the other, or, in some cases, that of a continuous liquid phase into which the organic polymer is dispersed in the form of polymer particles. The mixture of the compound according to any of structures I-IV and the organic polymer may form the disperse phase in an emulsion or dispersion in another material, which serves as a continuous liquid phase, as is the case with a latex.

The relative amounts of the compound of structures I-IV and the organic polymer may vary considerably. In various embodiments, the organic polymer may constitute from 10 to 99.9%, from 30 to 96%, from 65 to 90% or from 40 to 60% of the combined weight of polymer and compound of structure I-IV.

Compounds according to structures I-IV often perform a plasticizing function when blended with organic polymers. When a compound of structures I-IV is to perform such a function, it is preferably liquid at room temperature or, if a solid at room temperature, it has a glass transition temperature and/or softening temperature below room temperature, often 0° or –20° C. Plasticization is indicated by a reduction in $T_g$ of the composition, compared to that of the neat organic polymer, and or a softening or flexibilizing effect, as indicated by a reduction in Shore hardness and/or a lowered flexural modulus, respectively. Typically, the combination the organic polymer and the compound of any of structure I-IV will have a $T_g$ of at least 5° C. lower at least 15° C. lower, at least 30° C. lower, or at least 50° C. lower than a $T_g$ of the neat polymer, as measured by DSC according to ASTM D3418 or other DSC method. A useful general procedure is as follows: The sample is evaluated on a TA Q200 instrument with refrigerated cooling and TA Thermal Advantage software (TA Instruments; New Castle, Del.), or equivalent, using a ramp rate of 20° C./min. Samples are ramped from room temperature to 210° C. followed by a rapid quench. Samples are then reheated to 210° C. at a rate of 20° C./min. Glass transition temperature is measured on the second scan.

When used to perform a plasticizing function, a compound of any of structure I-IV preferably have viscosities less than about 500 centipoise (cP) at 25° C. The viscosity may be from about 1 cP to 250 cP; or about 50 cP to 200 cP at 25° C. Low viscosity provides ease of compounding into one or more polymer compositions without, for example, preheating, or addition of diluents or solvents to lower viscosity and enables the creation of pastes such as plastisols.

In certain embodiments, at least a portion of compound I-IV is in a liquid phase of the plastisol. As used herein, the term "plastisol" means a flowable suspension of polymer particles in a plasticized emulsion that forms a solid, flexible, plasticized polymer product with the addition of heat. A preferred polymer phase is polyvinylchloride) although other polymer particles can be used. A plastisol in accordance of the invention may contain from 10 to 90% by weight of a compound of structure I-IV. Polymer plastisols are, in embodiments, poured into a mold or onto a surface where the subsequent addition of heat causes the suspension to form a solid, flexible mass. In such embodiments, it is important for the plasticizer to cause "fusing", which means for the purposes of discussion that the polymer particle boundaries of the plastisol are broken by the effect of the plasticizer, causing mixing of the polymer on a molecular scale, wherein the effect persists to the solid state. Compounds according to structures I-IV are often function well as "fast fusing plasticizers," which means that they shorten the time required for the polymer particle boundaries of the plastisol to be broken and mixing to occur, lower the temperature required for the polymer particle boundaries of the plastisol to be broken and mixing to occur, or both.

Plastisols in accordance with the invention are useful in the production of sheet stock or films, flooring, tents, tarpaulins, coated fabrics such as automobile upholstery, in car underbody coatings, in moldings and other consumer products. Plastisols are also used in medical uses such as blood bags and multilayered sheets and films, tubing, footwear, fabric coating, toys, flooring products and wallpaper. Plastisols typically contain 40 to 200 parts by weight, more typically 50 to 150 parts by weight, more typically 70 to 120 parts by weight, more typically 90 to 110 parts by weight of plasticizer per 100 parts of dispersed polymer particles. PVC plastisols are usually made from PVC that has been produced by emulsion polymerization.

In certain embodiments, compounds according to structures I-IV are contained in a PVC plastisol composition containing from 40 to 200 parts by weight, or 50 to 150 parts by weight, or 70 to 120 parts by weight, or 90 to 110 parts by weight of the compound per 100 parts of PVC. Such plastisol compositions tend to have stable viscosities; their viscosities tend to increase less than about 200% over a period of 14 days when stored at a temperature between about 20° C. to 25° C., or less than about 100%, preferably less than 70% and more preferably less than 50% when stored at a temperature of between about 20° C. to 25° C. for five days.

In another embodiment of the present disclosure, a process for the production of flexible PVC articles is provided, whereby a layer is formed from a plastisol containing from 40 to 200 parts by weight, or 50 to 150 parts by weight, or 70 to 120 parts by weight, or 90 to 110 parts by weight of a plasticizer composition containing one or more of compounds I-IV per 100 parts by weight of PVC, and subsequently fusing the layer by the application of heat. A plastisol in accordance with the invention may further contain one or more additional plasticizers such as diethylene glycol dibenzoate, butyl benzyl phthalate, dibutyl phthalate, diisononyl phthalate, diisodecyl phthalate, other dialkyl phthalates, dipropylene glycol dibenzoate, such as the phenyl cresyl esters of pentadecyl sulfonic aromatic sulfonic acid esters available from Bayer AG of Leverkusen, Germany as MESAMOLL™, citrates such as tributylacetyl citrate, tri-2-ethylhexyl phosphate, trioctyl phosphate such as 2-ethylhexyl-isodecyl phosphate, di-2-ethylhexyl phenyl phosphate, triphenyl phosphate and tricresyl phosphate and the like.

In general, polymer compositions in accordance with the invention may further include one or more crosslinkers, adjuvants, colorants, antifouling agents, tougheners, solvents, fillers, metal particulates, odor scavenging agents, lubricants, thermal stabilizers, light stabilizers including UV stabilizers, flame retardant additives, pigments, blowing agents, processing aids, impact modifiers, coalescing solvents, or a combination thereof.

The useful, optional additives include, but are not limited to, trimethyl pentanyl diisobutyrate, dialkyl isophthalates, dialkyl terephthalates, alkyl benzyl phthalates, dialkyl adipates, trialkyl trimellitates, alkylyl trialkyl citrates, dialkyl azelates, dialkyl glutarates, dialkyl sebacates, dialkyl cyclohexanedicarboxylates, dialkyl sulfonates, esters of pentaerythritol, esters of glycerol, esters of fatty acids, glycol dibenzoates, epoxidized soybean oil, any of the additives described in International Patent Application Nos. PCT/US08/79337 or PCT/US09/40841, or a mixture of any of these additional additives. One or more of the alkyl, dialkyl, or trialkyl groups are, in embodiments, n-butyl, n-pentyl, n-hexyl, n-heptyl, n-octyl, n-nonyl, n-decyl, n-undecyl, n-dodecyl, capryl, cyclohexyl, 2-ethylhexyl, isobutyl, isopentyl, isohexyl, isoheptyl, isooctyl, isononyl, isodecyl, isoundecyl, or a mixture thereof. In embodiments, the alkylyl is acetyl or n-butyryl. In embodiments, the glycol is ethylene glycol, propylene glycol, diethylene glycol, or dipropylene glycol. The additional additives are present, in embodiments, as a blend with one or more of the compounds I-IV.

Still more, optional materials that may be present in a polymer composition of the invention include, for example, one or more solvents (including coalescing solvents), crosslinkers, colorants (dyes or pigments), antifouling agents (such as antifungal, antibacterial, or antiviral agents), tougheners, tackifiers, additional polymers, fillers, diluents, viscosity modifying agents, metal particulates, odor scavenging agents, adjuvants, lubricants, heat stabilizers, light stabilizers including UV stabilizers, flame retardant additives, blowing agents, processing aids, impact modifiers, or a combination thereof. The additional materials impart various elements of functionality to the composition, the nature of which depend on the intended use of the composition, for example in one or more articles as will be described below.

Polymer compositions of the invention are useful to form a variety of articles. An "article" as used herein is an item with a discrete shape, such as a tube, a film, a sheet, or a fiber, that incorporates one or more compositions of the disclosure; in some embodiments, the article may have its origin in a composition that undergoes a transformation, such as solidification or evaporation of one or more solvents, to result in the final article. In some embodiments, an article is substantially formed from a polymer composition of the invention; in other embodiments, the polymer composition of the invention forms only one part, such as one layer, of an article.

An article can be formed from a polymer composition of the invention by a wide range of fabrication methods, including for example, coating, casting, extrusion, coextrusion, profile extrusion, blow molding, thermoforming, injection molding, coinjection molding, reaction injection molding, milling, or weaving. Where the polymer includes PVC, for example, the article is, in some embodiments, a casing, a pipe, a cable, a wire sheathing, a fiber, a woven fabric, a nonwoven fabric, a film, a window profile, a floor covering, a wall base, an automotive item, a medical item, a toy, a packaging container, a screw closure or stopper adapted for a bottle, a gasket, a sealing compound, a film, a synthetic leather item, an adhesive tape backing, or an item of clothing. In some embodiments, the casing is a casing for an electrical device. In some embodiments, the medical item is medical tubing or a medical bag. In some embodiments, the film is a roofing film, a composite film, a film for laminated safety glass, or a packaging film. In some embodiments, the packaging container is a food or drink container. In some embodiments, the sealing compound is for sealed glazing. In some embodiments, the automotive item is seat upholstery, an instrument panel, an arm rest, a head support, a gear shift dust cover, a seat spline, a sound-deadening panel, a window seal, a landau top, a sealant, a truck tarpaulin, a door panel, a cover for a console and glove compartment, a trim laminating film, a floor mat, a wire insulation, a side body molding, an underbody coating, a grommet, or a gasket.

In some embodiments, the article comprises two or more layers and the compound of any of structures I-IV constitutes or is contained within at least one layer. In another embodiment, the article comprises a composition containing one or more compounds I-IV in at least one layer. In some such embodiments, the other of the two adjacent layers contains a plasticizer that doesn't have a structure corresponding to compounds I-IV; the plasticizers include, in various embodiments, other additives. Some examples of such additives include dialkyl phthalates, trimethyl pentanyl diisobutyrate, dialkyl isophthalates, dialkyl terephthalates, alkyl benzyl phthalates, dialkyl adipates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, epoxidized soybean oil, and mixtures thereof.

Certain polymer compositions in accordance with the invention are useful as adhesives, including as adhesive films or adhesive coatings. Such adhesives may include, for example, a poly(vinyl acetate) or vinyl acetate copolymer emulsion.

In some embodiments, the compounds I-IV are useful as plasticizers in nail polish formulations. In another embodiment, compounds I or II can be used as solvents and/or cosolvents in these formulations. Polymers useful in nail polish formulations include nitrocellulose, tosylamide-formaldehydes and the like.

Compounds according to any of structures I-IV are also useful as lubricants or as a component of a lubricant composition. In some embodiments, a blend or mixture of two or more such compounds are useful as lubricants or as components of a lubricant composition. The lubricant typically includes at least one antioxidant, which typically will constitute from 0.1 to 5, especially from 0.1 to 2% by weight of the lubricant composition. The lubricant is applied between two contacting surfaces to provide lubricating performance between the two surfaces.

Lubricants in accordance with the invention are useful as, for example, such as compressor fluids, industrial oils (anti-wear, circulating, compound, cotton picker, cylinder, edge coat seal, electrical, biodegradable lubricants), engine oils, automatic transmission fluids, automotive gear lubricants, metalworking fluids, and R&O turbine oils. Compounds I-IV of the present disclosure can be used as a blend with one or more other lubricants, such as, for example, one or more mineral oils, polyalphaolefins, dibasic esters, polyol esters, alkylated aromatics, polyalkylene glycols, phosphate esters, vegetable oils, and the like. Lubricant formulations can further include antiwear and extreme pressure agents, corrosion and rust inhibitors, detergents, dispersants, friction modifiers, pour point depressants, seal swell agents, viscosity modifiers, antifoam agents, metal deactivators, and the like, pour point of the product of Example 5 is evaluated according to (Foaming Characteristics—Sequences I, II and II), and ASTM D97, respectively.

Compounds I-IV useful as lubricants or in lubricant formulations preferably have a pour point, as measured according to ASTM D97, of no higher than 0° C., preferably no higher than −20° C. The compounds preferably exhibit excellent resistance to foaming, as indicated by ASTM D892 IP 146, and preferably exhibit foam volumes of less than 1 mL after both 5 and 10 minutes of blowing on that test. Low foaming can give a better lubricating film and steady oil pressure during extensive operations. Further, low foam lubricants can lead to better performance in high performance oil pump systems with high volume or pressure.

The following examples further elucidate and describe the compounds of the disclosure and applications thereof without limiting the scope thereof. All parts and percentages are by weight unless otherwise indicated.

EXAMPLE 1

A 250 mL 3-neck round bottom flask is charged with 32.8 g (0.15 mol) of the glycerin ketal of ethyl levulinate (Et-LGK) (98.2%), and 91.0 g (0.45 mol) of the 1,2-propylene glycol ketal of ethyl levulinate (Et-LPK) (0.14% ethyl levulinate and no detectible propanediol). The contents of the flask are stirred under vacuum (6 torr) and heated to 110° C. and 9.7 µL of a titanium tetra-isopropoxide is added into the flask. A nitrogen purge is maintained and the contents of the flask are heated to 230° C. during which time a liquid condensate forms. The reaction mixture is cooled to 110° C., and distillation of a second liquid is accomplished using reduced pressure of about 4 torr.

The reaction mixture is allowed to cool to ambient temperature when no further distillate is collected. The product is a mixture of compounds corresponding to structure III in which a and c are 2, b is 0, d is 0, i is 1, $R^1$ and $R^8$ are methyl, $R^3$ is $CH(CH_3)$, $R^4$ is methylene, $R^7$ is hydrogen and $R^{23}$ is ethyl. The value of n is 1 for about 48.6% of the material, 2 for 26.8% of the material, 3 for 12.2% of the material and 4 for 8.2% of the material. The product contains 4.3% of residual Et-LGK and Et-LPK.

EXAMPLE 2

A 250 mL 3-neck round bottom flask is charged with 18.02 g (0.2 mol) of 1,4-butanediol ((BDO) Sigma Aldrich Company, St. Louis, Mo.) and 121.35 g (0.6 mole) of ethyl-LPK (Et-LPK) (0.14% ethyl levulinate and no detectible propanediol). The contents of the flask are stirred at a pressure of 6 torr while heating to 90° C. Then 3.22 µL of a titanium tetra-isopropoxide is added into the flask. A nitrogen purge is maintained and the contents of the flask are heated to 200° C. for 3 hours, during which time a condensate forms. The reaction mixture is allowed to cool to 110° C., and distillation of a second liquid is accomplished under reduced pressure of about 7 torr. The reduced pressure is maintained until no further distillate is collected. The flask is allowed to cool to ambient temperature and the pressure is equilibrated to atmospheric pressure.

The reaction product contains about 87.2% of the compound corresponding to

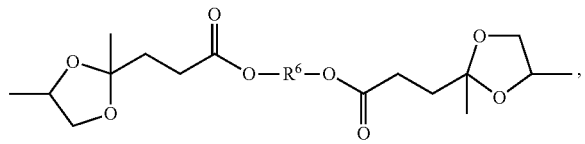

about 1.1% of the compound corresponding

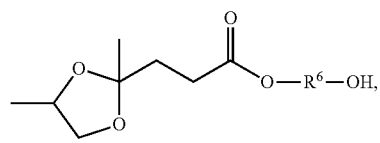

wherein $R^6$ is —$(CH_2)_4$— and about 0.6% of ethyl-LPK. The product also contains some oligomerized materials.

EXAMPLES 3-4 AND COMPARATIVE SAMPLE 1

The product of Example 1 is pre-mixed with poly(vinyl chloride) ((PVC), $M_n$=55,000, Mw=97,000) at 50 parts plasticizer per hundred parts PVC. The premix is separately blended for 10 minutes in a twin screw extruder operated at 165° C.-170° C. under a continuous nitrogen (N2) purge to form Example 3. Example 4 is made in the same manner, except that the product of Example 2 replaces the product of Example 1.

Shore A Hardness of the resulting blends is measured according to ASTM D 2240. $T_g$ is measured using standard DSC techniques. Example 3 has a $T_g$ of −9.7° C. and a Shore A hardness of 81.5. Example 4 has a $T_g$ of −8.0° C. and a Shore A hardness of 78.8. The PVC by itself has a $T_g$ of 67.2° C.

EXAMPLE 5

A 5-gallon Parr Model 4557 reactor (Parr Instrument Co., Moline, Ill.) is charged with 12.74 kg (63 moles) of Et-LPK and 1.89 kg (20.97 moles) 1,4-butanediol (Sigma-Aldrich Company; St. Louis, Mo.). The contents of the reactor are stirred at 50 rpm at a pressure of 52 torr; the recirculating chiller is operating at −10° C. and the high temperature circulator is operating at 70° C. The reaction mixture is purged with dry nitrogen for about 16 hours. Then, a vacuum of 4-5 Torr is applied to the reactor for about 2 hours. 0.358 g (1.26 mmoles) titanium (IV) isopropoxide (Sigma-Aldrich Company, St. Louis, Mo.) is admixed with 4 mL of Et-LPK and added to the reactor. The reaction mixture is purged for about 20 minutes with dry nitrogen followed by the high temperature circulator set at 200° C.

The contents of the reactor are heated to about 200° C. for 3 hours, during which time a condensate is collected. At about 97.2% conversion, the reactor is cooled with an applied vacuum of 20-25 torr, by reducing the high temperature circulator set point to 200° C. Distillation is continued by applying a vacuum of about 5 Torr to the reactor until condensate formation is discontinued. The contents of the reactor are analyzed by GC-FID. Distillation is then restarted and continued as described above until subsequent analysis reveals that the concentration of ethyl-LPK is less than about 1.0%. When distillation is complete, the reactor is cooled to ambient temperature.

The reaction product contains about 90.77% of a material according to structure I in which a is 2, b is 0, x is 1, y is 1, $R^1$ is —$CH_3$, $R^3$ is $CH(CH_3)$, $R^4$ is methylene, $R^6$ is —$(CH_2)_4$—, and each Z is —O—.

EXAMPLE 6

A 5-gallon reactor is charged with 12.54 kg (62 moles) Et-LPK, 3.38 kg (15.48 moles) of Et-LGK, and 2.95 g IRGAFOS® 168 (Ciba AG, Basel, Switzerland). The contents of the reactor are stirred at 50 rpm at a pressure of 52 torr with the recirculating chiller set to −10° C.; the high temperature circulator operating at 70° C. overnight for about 16 hours. A vacuum of 4-5 torr is applied to the reactor for about 2 hours. 0.358 g (1.26 mmoles) titanium (IV) isopropoxide is admixed with 4 mL of Et-LPK and added to the reactor. The reaction mixture is then purged for about 20 minutes with dry nitrogen and the high temperature circulator set at 200° C.

The contents of the reactor are heated to about 200° C. for 6 hours, and a condensate is collected. After the reaction has reached about 99.0% conversion Et-LPK AN Et-LGK distilled off until their combined concentration is less than 1%. When distillation is complete, the reactor is cooled to ambient temperature. The product is a mixture of compounds according to structure III in which a and c are 2, b is 0, d is 0, i is 1, $R^1$ and $R^8$ are methyl, $R^3$ is $CH(CH_3)$, $R^4$ is methylene, $R^7$ is hydrogen and $R^{23}$ is ethyl. Species in which n is 1, 2, 3, or greater than 3 respectively constitute 49.60%, 28.35%, 13.01% and 8.32% of the composition.

EXAMPLES 7-8

100 parts of a suspension grade PVC powder (Type 2095 Georgia Gulf Corporation, Atlanta, Ga.) are blended with 2.5 parts of a stabilizer (ThermChek-SP175, Ferro Corporation, Cleveland, Ohio) and then with 5 parts of epoxidized soybean oil.

The resulting mixture is then blended with 50 parts of the product of Example 5 to form Example 7. Blending is performed on an orbital mixer for about 5 minutes. The mixture is transferred into the feed hopper of a 27 mm BRABENDER® (model #DR2051) PolySpede twin-screw extruder (CW. BRABENDER® Instruments, Inc., South Hackensack, N.J.). The material is extruded at 150° C. with a screw speed of 65 rpm through a 2 mm rod die. The material is cooled by a water bath and fed into a Brabender pelletizer.

Example 8 is prepared in the same way, using the product from Example 6 instead of the product of Example 5.

Pelletized extrudates are fed into a Nissei injection molding machine (Model #PS04E5A; Nissei-America, Inc., Gahanna, Ohio). ASTM D638-90 Type I tensile bars are injection molded at the following conditions: 165° C. set temperature for heating zones 1-3, 165° C. set temperature for the injection nozzle, 25° C. mold temperature, 25% screw speed, 53 mm shot size, 5% back pressure, 1.17 second mold fill time and 9 second recovery time, followed by 15 seconds cooling before removing the tensile bar from the mold.

Plasticizer loadings in the molded tensile bars are determined using weight loss data from thermogravimetric analysis (TGA) using a TA Q50 with TA Thermal Advantage software (TA Instruments; New Castle, Del.). Analysis is carried out by equilibrating the samples at 30° C. followed by a temperature ramp of 10° C./min to 600° C. The results of analysis, labeled "Actual Wt. % Plasticizer" are shown in Table 1.

Glass transition temperature ($T_g$) of the pelletized extrudates is determined by following ASTM D-3418, employing a TA Q200 instrument with refrigerated cooling and TA Thermal Advantage software. Homogeneous samples in a range of about 5 and 15 mg are placed in a T-zero pan and crimped with a T-zero lid. $T_g$ values are shown in Table 1.

Shore A hardness testing is carried out at the ends of the molded tensile bars, where the outer width is wider than the gauge width with a Durometer Type A (Instron, Norwood, Mass.) as specified by ASTM D2240, except that the sample thickness of the molded tensile bars in the area of testing is 3.2 mm; readings are taken after 15 seconds. An average of ten readings is taken per sample and reported in Table 1.

Extraction of soluble materials is carried out in both hexanes and a 1% solution of soap in water. Hexane (Fisher Scientific, Waltham, Mass.) was used as received. The 1% soap water solution is made using deionized water and IVORY® soap shavings (Procter and Gamble Co., Cincinnati, Ohio). Five molded tensile bars are tested and the average value is recorded for each. Pre-extraction and post-extraction mass measurements are obtained on the molded tensile bars. The molded tensile bars are completely immersed (hanging in the container) in the extraction media at ambient temperature. After 24 hours of immersion, the samples are removed from the extraction media; the soap solution samples are rinsed with deionized water before being allowed to dry. All samples are air dried for 24 hours before post-extraction mass is measured. The weight loss of the samples is reported in Table 1.

TABLE 1

| Example | Actual Wt. % Plasticizer (TGA)/Source | $T_g$, (° C.) | shore A Hardness | Wt. % loss, 24 hr in hexane | Wt. % loss, 24 hr in 1% soap solution |
|---|---|---|---|---|---|
| 7 | 30 (Ex. 5) | 5 | 89 | 0 | 0 |
| 8 | 33 (Ex. 6) | 7 | 93 | 0 | 0 |

EXAMPLES 9-12

Examples 9-12 are separately made, all in the following manner 250 ml 4-neck round bottom flask is charged with 43.62 g (0.2 mol) of Et-LGK, and 80.90 g (0.4 mol) diethyl adipate (DEA), followed by the addition of 0.0063 g Irgafos® 168 (Ciba Corporation; Florham Park, N.J.). The contents of the flask are stirred under a nitrogen blanket at 60° C. 12 μl (microliters) of Ti(isopropoxide)$_4$ is added to the flask. The contents of the flask are heated to 110° C., degassed for about 5 minutes at 3-5 torr, and back-filled with nitrogen. The reaction mixture is heated to 230° C. and a condensate is distilled from the reaction until completion. The flask is cooled to ambient temperature. The reaction mixtures are purified by vacuum distillation to remove residual starting materials.

The products in each case are mixtures of compounds according to structure IV, in which e is 2, f is 0, i is 1, $R^{10}$ is ethyl, $R^{12}$ is —$(CH_2)_4$—, $R^{14}$ is methyl and $R^{15}$ is hydrogen. Each of Examples 9-12 contains species in which s is 1, v is 0 and w is 1, species in which s is 1, v is 0 and w is 2 or s is 1, v is 1 and w is 1 and species in which s is 1, v>1 and w>2. They all contain unreacted starting materials. The relative amounts of those species are indicated in Table 2.

TABLE 2

| Example | s is 1, v is 0 and w is 1, % | s is 1, v is 0 and w is 2 or s is 1, v is 1 and w is 1, % | s is 1, v > 1 and w > 1, % | Unreacted starting materials, % |
|---|---|---|---|---|
| 9 | 49 | 23 | 28 | 0.4 |
| 10 | 58 | 23 | 18 | 1.5 |
| 11 | 42 | 25 | 32 | 1.2 |
| 12 | 48 | 18 | 8 | 24 |

EXAMPLE 13

A 500 mL 4-neck round bottom flask is charged with 191.91 g (0.95 mol) DEA and 62.30 g (0.24 mol) of the trimethylolpropane ketal of ethyl levulinate (Et-LTMPK). Et-LTMPK is synthesized according to the procedure outlined in WO 2007/062118. The reaction mixture is heated to 60° C. with a nitrogen purge for 12 hrs. 16 μL of TPT is added to the flask, followed by heating the mixture to 110° C. At 110° C., a vacuum of 20 torr is applied for 5 min and back-filled with nitrogen, and the reaction temperature is increased to 230° C. A liquid condensate is collected with the temperature gradually increasing to 260° C. After about 3 hours, the contents of the flask are cooled to ambient temperature.

The product corresponds to structure IV in which e is 2, f is 1, i is 1, $R^{10}$ is ethyl, $R^{12}$ is —$(CH_2)_4$—, $R^{14}$ is methyl and $R^{15}$ is ethyl. Example 13 contains 54.6% of species in which s is 1, v is 0 and w is 1, 11.2% of species in which s is 1, v is 0 and w is 2 or s is 1, v is 1 and w is 1 and 3.2% of species in which s is 1, v>1 and w>2.

EXAMPLE 14

A 250 mL 3-neck round bottom flask is charged with 26.63 g (0.13 mol) of the glycerin ketal of ethyl acetoacetate (synthesized according to WO 2007/062118), 105.37 g (0.52 mol) diethyl adipate, and heated to 60° C. for 12 h under nitrogen purge, then increasing the temperature to 110° C. and a pressure of 20 Torr for an additional 2 hours. Then 7.5 μL of titanium (IV) isopropoxide is added to the flask, and refilled with nitrogen; the flask is heated to 230° C. for 2.5 hours, followed by an increase in temperature to 240° C. for an additional 2 hours. The mixture is cooled to ambient temperature. The product is purified by distilling off unreacted starting materials at 8 Torr and 125° C. for about 25 minutes.

The product corresponds to structure IV in which e is 1, f is 0, i is 1, $R^{10}$ is ethyl, $R^{12}$ is —$(CH_2)_4$—, $R^{14}$ is methyl and $R^{15}$ is hydrogen. Example 14 contains 36.7% of species in which s is 1, v is 0 and w is 1, 19.4% of species in which s is 1, v is 0 and w is 2 or s is 1, v is 1 and w is 1 and 31.1% of species in which s is 1, v>1 and w>2.

EXAMPLES 15-16

A 250 ml 4-neck round bottom flask is charged with 49.08 g (0.225 mol) of Et-LGK and 78.39 g (0.45 mol) diethyl succinate ((DESU) Sigma Aldrich; St. Louis, Mo.), and heated to 60° C. under a constant nitrogen purge for 12 hours to dry the starting materials. 13.5 μl of TPT is added to the reaction flask and the reaction mixture is heated to 110° C. for 25 minutes, followed by degassing under a vacuum of 5-8 torr for 5 minutes; back-filling the flask with nitrogen, and heating to 210° C. A condensate is collected and monitored to determine the percent conversion of the reactants to products. The product (Example 15) corresponds to structure IV in which e is 2, f is 0, i is 1, $R^{10}$ is ethyl, $R^{12}$ is —$(CH_2)_2$—, $R^{14}$ is methyl and $R^{15}$ is hydrogen. Example 15 contains 52% of species in which s is 1, v is 0 and w is 1, 30% of species in which s is 1, v is 0 and w is 2 or s is 1, v is 1 and w is 1 and 17% of species in which s is 1, v>1 and w>2.

Example 16 is made in the same manner, except the amount of Et-LGK is doubled and the reaction time is extended to 45 minutes. The product corresponds to structure IV in which e is 2, f is 0, i is 1, $R^{10}$ is ethyl, $R^{12}$ is —$(CH_2)_2$—, $R^{14}$ is methyl and $R^{15}$ is hydrogen. Example 16 contains 69% of species in which s is 1, v is 0 and w is 1, 24% of species in which s is 1, v is 0 and w is 2 or s is 1, v is 1 and w is 1 and 7% of species in which s is 1, v>1 and w>2.

EXAMPLES 17-18

Et-LGK and diethyl sebacate ((DESE), Sigma Aldrich; St. Louis, Mo.) are reacted similarly in the procedure described for Examples 15-16 above. The reaction temperature is 230° C., the reaction time is 46 minutes for Example 17 and 35 minutes for Example 18. The ratio of Et-LGK to diethyl sebacate is 2:1 in Example 17 and 4:1 in The Example 17 product corresponds to structure IV in which e is 2, f is 0, i is 1, $R^{10}$ is ethyl, $R^{12}$ is —$(CH_2)_8$—, $R^{14}$ is methyl and $R^{15}$ is hydrogen. It contains 45% of species in which s is 1, v is 0 and w is 1, 32% of species in which s is 1, v is 0 and w is 2 or s is 1, v is 1 and w is 1 and 21% of species in which s is 1, v>1 and w>2.

The Example 18 product corresponds to structure IV in which e is 2, f is 0, i is 1, $R^{10}$ is ethyl, $R^{12}$ is —$(CH_2)_8$—, $R^{14}$ is methyl and $R^{15}$ is hydrogen. It contains 73% of species in which s is 1, v is 0 and w is 1, 20% of species in which s is 1, v is 0 and w is 2 or s is 1, v is 1 and w is 1 and 6% of species in which s is 1, v>1 and w>2.

EXAMPLES 19-21

Examples 19-21 are prepared as follows. 100 parts of a suspension grade PVC powder type (Type 2095 Georgia Gulf Corporation) are blended with 2.5 parts of a stabilizer (ThermChek-SP175), and then with 5 parts of epoxidized soybean oil. The product of Example 9 is added at a predetermined loading, and mixed in a Kitchen-aid mixer with a paddle blade for approximately 5 minutes. The powder is transferred into a feed hopper of a 27 mm Brabender twin-screw extruder at 150° C. All materials are passed through a 2 mm rod die, and cooled by a water bath and pelletized. Pelletized material is fed into a Nissei injection molder, with three heating zones and a nozzle temperature of 165° C. The mold temperature is set at 25° C. The screw speed is set at 30% with a shot size of 5 mm and a 5% back pressure is used to fill the mold with a mold fill time of 1.01 sec, and recovery time of 11.5 sec.

Glass transition temperature is determined for each of Examples 19-21 according to ASTM D-3418. Tensile properties are measured according to ASTM D638. Shore A Hardness is measured at 15 seconds (ASTM D2240) on injection molded bars with a 3.2 mm thickness. Results are as indicated in Table 3.

TABLE 3

| Example | Plasticizer Loading (phr) | $T_g$ (° C.) | Elongation at Break (%) | Secant Modulus at 100% (MPa) | Shore A Hardness |
|---|---|---|---|---|---|
| 19 | 30.0 | 13 | 204 | 19.8 | 98 |
| 20 | 50.0 | −16 | 332 | 7.9 | 84 |
| 21 | 70.0 | −25 | 338 | 4.7 | 74 |

Extractions (described in Examples 7-8) in hexane, soap water, and mineral oil are conducted on each of Examples 19-21 according to ASTM D 1239 with the following modifications. Samples are not preconditioned, 1.4 L containers are used for extractions, and 5 replicate samples are immersed in the same container. Extraction results are presented in Table 4.

TABLE 4

| | Plasticizer | Weight Loss (%) | | |
|---|---|---|---|---|
| Example | Loading (phr) | Hexane | 1% Soap in Water | Mineral Oil |
| 19 | 30 | 0 | 0 | 0 |
| 20 | 50 | 0.1 | 0.2 | 0.1 |
| 21 | 70 | 0.5 | 0.5 | 0.4 |

EXAMPLES 22-23 AND COMPARATIVE SAMPLE 2

Poly(lactic acid) (PLA) resin (grade 4060D; Nature Works, LLC; Minnetonka, Minn.) is dried at 40° C. under vacuum for 4 hours prior to compounding. The PLA is compounded with the product of Example 12 in a Brabender 3-piece bowl mixer at 210° C. set at 60 rpm. The PLA resin is fed into the bowl mixer with mixing for 2 minutes, followed by adding the Example 12 product with mixing for an additional 8 minutes. For Example 22, 10% by weight of the Example 12 product is added; for Example 23, 20% by weight of the Example 12 product is added. In Comparative Sample 2, no plasticizer is added. The compounded samples are dried under vacuum at 40° C. for 4 hours. A Carver Model 4122 pneumatic heated plate press (Carver, Inc.; Wabash, Ind.) is preheated to 210° C. Samples are heated without pressure on a pneumatic heated plate press at 210° C. for 5 minutes, followed by pressing at 5000 lbs force for 5 minutes. The samples are quenched in a water bath and allowed to warm to room temperature. All moldings are transparent water-white films having a thickness of approximately 0.075 mm.

Migration of the plasticizer from compounded samples is measured using the following procedure: 1 inch squares of compounded melt pressed films are marked with blue, red, and black Sharpie® markers; the samples are placed in a controlled heat and humidity chamber at the conditions specified, and changes to the ink are evaluated after 100 days. Migration behavior on a scale of 1 to 5 is used (i.e., 1 (none) being no change in the ink, 2 (very slight) being a small change to the ink edges), 3 (slight), being a running of the ink edges, 4 (clear) being slight oiliness on the surface to the touch, and 5 (very clear) being visible oil on the surface). Migration results are reported in Table 5.

Glass transition temperature ($T_g$) is determined using the general procedure described above; results are as reported in Table 5.

TABLE 5

| Designation | Wt. % Plasticizer | $T_g$ (° C.) | Migration 40° C. dry 100 days | Migration 25° C. and 50% RH 100 days |
|---|---|---|---|---|
| Comp. 2 | 0 | 57 | NA | NA |
| 22 | 10 | 39 | 2 | 2 |
| 23 | 20 | 23 | 2 | 2 |

EXAMPLES 24-25 AND COMPARATIVE SAMPLE 3

10 parts of Ultra Talc 609 ((Talc) Specialty Minerals; Bethlehem, Pa.) are premixed with 100 parts of poly(lactic acid) resin ((PLA) grade 4032D; Nature Works, LLC; Minnetonka, Minn. This premix is compounded in a Brabender 3-piece bowl mixer at 210° C., and mixed at 60 rpm for 10 minutes to form a talc filled master batch. The master batch is cooled and ground. The master batch is dry blended with virgin PLA resin (grade 4021D; Nature Works, LLC; Minnetonka, Minn.) at ratios such that the dry blend contains 1% by weight talc. This dry blend is compounded with the product of Example 12 in the Brabender at 210° C. Glass transition temperature ($T_g$) and melting temperature (Tm) are determined following the procedure outlined in Examples 22-23 above. Cooling crystallization temperature ($T_c$) is determined using the following method: samples are ramped at 20° C./min from room temperature to 210° C. followed by a rapid quench, a second ramp is then performed from 25° C. to 210° C. at 20° C./minute followed by a cooling ramp from 210° C. to 25° C. at 10° C./min, cooling crystallization temperature ($T_c$) is determined as the crystallization peak maximum during the cooling scan. Thermal measurements and migration results are listed in Table 6.

TABLE 6

| Designation | Wt. % Plasticizer | $T_g$ (° C.) | $T_m$ (° C.) | Cooling $T_c$ (° C.) | Migration 40° C. dry | Migration, 25° C. and 50% RH |
|---|---|---|---|---|---|---|
| C3 | 0 | ND | 158 | 81 | NA | NA |
| 24 | 10 | 18 | 164 | 76 | 1 | 3 |
| 25 | 20 | 14 | 161 | 81 | 1 | 1 |

EXAMPLES 26-33

Examples 26-33 are prepared as follows. 100 parts of a suspension grade PVC powder type (Type 2095 Georgia Gulf Corporation) are blended with 1.5 parts of a stabilizer (ThermChek-SP 175), and then with 2.5 parts of epoxidized soybean oil. The products of Examples 9, 10, 12, 14-18, respectively are used as plasticizers in Examples 26-33. Plasticizer is added at 50 phr, and blended by hand prior to feeding into a HAAKE PolyLab extruder (Thermo Scientific; Waltham, Mass.). The mixture is melt mixed at 165° C. with co-rotating screws at 150 rpm for 10 minutes. The compounded PVC mixtures are melt pressed in a Carver Model 4122 pneumatic heated plate press (Carver, Inc.; Wabash, Ind.) to a thickness of 1 mm at 165° C. Samples are allowed to heat without pressure for 5 minutes. Pressure is applied and released stepwise: 1000 lbs force, 2500 lbs force, 4000 lbs force. Samples are pressed at 5000 lbs force for 1 minute. Samples are quenched in a water bath and allowed to come to room temperature. All materials are transparent water-white to light yellow colored films with no tackiness at the surface.

Shore A hardness is measured on a stack of films with a total thickness of 3 mm following the procedure outlined in Examples 19-21. Hexane extractions are performed on pre-weighed one inch squares of 1 mm thickness submersed in 6 mL of hexane for 24 hours at room temperature. The samples are then removed, patted dry, and allowed to equilibrate for 24 hours. Samples are weighed to determine the % mass loss. Thermal, hardness and extraction results are listed in Table 7.

TABLE 7

| Example | Plasticizer | Shore A Hardness | $T_g$ (° C.) | Mass Loss in Hexane (%) |
|---|---|---|---|---|
| 26 | Example 14 | 69 | −27 | 6 |
| 27 | Example 12 | 79 | −4 | 1 |
| 28 | Example 15 | 75 | −23 | 3.6 |
| 29 | Example 16 | 78 | −16 | 2 |
| 30 | Example 17 | 74 | −29 | 10 |
| 31 | Example 18 | 72 | −29 | 9 |
| 32 | Example 9 | 77 | −17 | 3 |
| 33 | Example 10 | 81 | −17 | 2 |

EXAMPLES 34-35

Polyvinyl acetate (PACE 383 Forbo Adhesives) is melt blended with the product of Example 11 at a 90:10 weight ratio. Viscosity is measured with a Brookfield RVT viscometer at 20 rpm and 25° C. The resulting plasticized polyvinyl acetate mixture is designated Example 34. Example 35 is made by melt blending 90 parts of a vinyl acetate ethylene copolymer (Duroset E-200 HV, Celanese Corporation) with 10 parts of the Example 11 product. The viscosities of the resulting blends are measured at 25° C. after blending, and again after 7 days at about 25° C. Example 34 exhibits an initial viscosity of 6040 cps and a viscosity of 6420 cps after 7 days. Example 35 exhibits an initial viscosity of 5500 cps and a viscosity of 5600 cps after 7 days.

Dried film properties are observed after applying a 1.6 mil wet film with a #16 wire wound rod onto glass plates. Glass plates are submerged in water to determine water resistance. Speed of set is measured by applying a 1.6 mil wet film with a #16 wire wound rod to Kraft paper. A second sheet of Kraft paper is applied to the top of the adhesive film. Set time is evaluated as the time before fiber tear is observed upon pulling off the top layer of Kraft paper. All materials have a similar speed of set. Open time is evaluated by applying a 1.6 mil wet film with a #16 wire wound rod to Kraft paper. Copy paper is laid over the adhesive film at 5 second intervals. The adhesive layer is allowed to dry overnight. The paper strips are peeled apart looking for fiber tear. The open time is defined as the time between laying the wet film, and the first interval where the fiber tear is observed Example 34 forms a tough, flexible film with no surface tack. Open time is 20 seconds. The films blush quickly and redisperse in water. Example 35 forms a soft flexible film with surface tackiness. Open time is 35 seconds. The films blush but do not redisperse.

For comparison, Example 34 is repeated twice, substituting a commercially available plasticizer (Benzoflex® LA-705 and Benzoflex® 50, both from Genovique, Rosemont, Ill.) for the Example 11 material. Each provides similar results to Example 34.

As a further comparison, Example 35 is repeated twice, substituting the Benzoflex® 50 material or dibutyl phthalate for the Example 11 product. Again, very similar results are obtained.

EXAMPLE 36

Levulinic acid (580.2 g, 5.0 mol), 1,3-propanediol (209.5 g, 2.75 mol), and sulfuric acid (39.5 mg, 22 µL, 50 ppm) are added to an empty 2-liter, 4-neck round bottom flask with stirring under nitrogen for 2 hours at 170° C. After 78% of the theoretical volatiles are collected, the reaction mixture is placed under reduced pressure. After 48 minutes, 97% of the theoretical volatiles are collected. The crude reaction mixture is cooled to room temperature.

The crude reaction mixture (390.95 g (1.44 mol)) and 1,2-propylene glycol (328.4 g, 4.3 mol; Brenntag) are added to 1-liter, 3-neck round bottom flask and heated to 70° C. with stirring at 10 torr vacuum for 4 hours. After 4 hours, 85% (44 mL) of the theoretical volatiles are collected, and propylene glycol (93.2 g, 1.22 mol) and sulfuric acid catalyst (18 mg, 10 μL) are added; the reaction mixture is stirred at 80° C. under 8 torr vacuum for an additional 4 hours. The remaining volatiles (100 mL) are collected and the reaction is cooled to room temperature. The crude product is neutralized with 20 g of dibasic sodium phosphate and filtered. The neutralized filtrate is purified by distillation and hexane extraction to yield 297.4 g of a compound having the structure

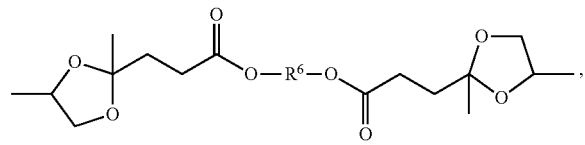

where $R^6$=—$(CH_2)_3$—.

EXAMPLE 37

A 100 mL 3-neck round bottom flask is charged with 7.61 g (0.1 mol) of 1,3-propanediol ((PDO) Sigma Aldrich Company; St. Louis, Mo.) and 44.50 g (0.22 mol) of Et-LGK. The contents of the flask are stirred at a pressure of 5 torr with heating to 90° C., and back-filled with nitrogen. 1.56 μL of titanium tetra-isopropoxide is added to the flask with a nitrogen purge; the contents of the flask are then heated to 200° C. After about 2.5 hours, the reaction mixture is allowed to cool to 104° C., and a second liquid is distilled under reduced pressure at about 5 torr. Reduced pressure is maintained until no further distillate is collected. The flask is allowed to cool to ambient temperature and atmospheric pressure.

The product contains about 80.9% of a compound having the structure

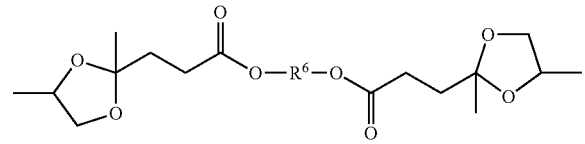

and about 3.0% of a compound having the structure:

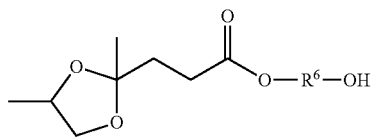

where $R^6$ in each case is —$(CH_2)_3$—.

EXAMPLES 38-39 AND COMPARATIVE SAMPLE 4

4.65 g of polylactic acid (PLA) (PLA 6062; NatureWorks LLC, Minnetonka, Minn.) is fed into a twin screw compounder (Haake MiniLab II, Thermo Scientific) at 200° C.; the compounding screws were co-rotating at 150 rpm. 0.35 g of the product from Example 5 is added drop-wise to the melted PLA in the compounder and blended for 10 minute; the extrudate is extruded through the die face and collected. The product is designated Example 38. Example 39 is made the same way, except that the product of Example 6 is substituted for the product of Example 5. Comparative Sample 4 is made the same way, but without any plasticizer. Comparative Sample 4 (neat PLA resin) exhibits a $T_g$ of 57° C. and a $T_m$ of 162° C. Example 38 exhibits a $T_g$ of 549° C. and a $T_m$ of 163° C. Example 39 exhibits a $T_g$ of 51° C. and a $T_m$ of 163° C.

EXAMPLE 40

The foaming tendency and pour point of the product of Example 5 is evaluated according to ASTM D892 IP 146 (Foaming Characteristics—Sequences I, II and II), and ASTM D97, respectively. The foam volume (ml) is determined at the end of a 5 minute and a 10 minute blowing period. Foam volumes of 0 ml are reported in all cases. Pour point is −33° C.

EXAMPLE 41

A 250 mL 3-neck round bottom flask is charged with Et-LPK (40.42 g, 0.20 mol), ethylenediamine (67 mL, 1.00 mol), and ethylene glycol (10 μL). The contents of the flask are heated to 120° C. for 40 minutes, at 130° C. for 15.25 hours, and at 140° C. for 6.74 hours. The reaction mixture is cooled to room temperature. The crude product contains 78% of the 1:1 adduct of Et-LPK: ethylenediamine and 12.5% of the 2:1 adduct of Et-LPK: ethylenediamine.

EXAMPLE 42

A 3-neck round bottom flask is charged with 1258.28 gm (5.76 moles) Et-LGK, and 198.26 gm (2.2 moles) 1,4-butanediol. The contents of the flask are heated to 70° C. for 16 hrs, and backfilled with nitrogen. 73.5 μL (0.25×10³ moles) of titanium isopropoxide is added to the reaction mixture with a nitrogen purge; the contents of the flask are heated to 200° C. for 6 hrs. A condensate is collected, and when 298.9 gm of the condensate is collected, the reaction is cooled and analyzed by GPC and $^1$H NMR. The product is a yellow viscous liquid. The product is a mixture of compounds that correspond to structure II, wherein e is 2, f is 0, x is 2, z is zero, $R^5$ is hydrogen, $R^6$ is —$(CH_2)_4$—, $R^{14}$ is methyl and $R^{15}$ is hydrogen. The mixture contains about 14% of species having a molecular weight of about 1375, 13% of species having a molecular weight of about 894, 21.5% of species having a molecular weight of about 682, 30% of species having a molecular weight of about 478, 19% of species having a molecular weight of about 303 and a small amount of residual Et-LGK.

EXAMPLE 43

A 3-neck round bottom flask is charged with 129.68 gm (0.28 moles) of the reaction product of Example 42 and 170.32 gm (0.84 moles) of ethyl 4-(2-methyl-1,A-dioxolan-5-yl)pentanoate. The contents of the flask are heated to 70° C. under a nitrogen purge for 16 hrs. 11 μL (0.37×10³ moles) of titanium isopropoxide is added to the reaction mixture with a nitrogen purge; the contents of the flask are heated to 210° C. for 20 hrs. 25.2 g of a condensate is collected and excess monomer is removed under vacuum at 200° C. for 3 hrs.

Examples 44-46 and Comparative Sample 4 Plasticizer migration out of PVC disks into activated carbon is determined according to ASTM D1203-A4. Tests are performed on 0.5 mm and 1.0 mm thick disks; conditions are 24 hours at 70° C. Butyl benzyl phthalate is the plasticizer for Comparative Sample 4. The product of Example 6 is used as the plasticizer in Example 44; the product of Example 5 is used as the plasticizer in Example 45; and the product of Example 43 is used as the plasticizer in Example 46. Loss of mass on this test indicates migration out of the sample; therefore, smaller absolute values indicate better results. Results are as reported in Table 8.

TABLE 8

| Plasticizer | Mass Change Activated Carbon, wt-%, 0.5 mm thick disk; | Mass Change Activated Carbon, wt-%, 1.0 mm thick disk; |
|---|---|---|
| Comparative Sample 4 | −2.64 | −1.81 |
| Example 44 | −1.33 | −0.88 |
| Example 45 | −1.41 | −0.99 |
| Example 46 | −0.88 | −0.52 |

EXAMPLES 47-48

62.5 wt % of PVC-2095, 1.9 wt % of ThermChek-SP1363, 3.1 wt % epoxidized soybean oil (ESO), 3.1 wt % ethyl laurate, 1.9 wt % texanol-isobutyrate, and 27.5 wt % plasticizer ((Example 5) for Example 47 and (Example 6) for Example 48) are formulated by blending with a Kitchen-Aid mixer on low speed for 2 min while slowly adding the plasticizer. Once a paste is formed, the composition is stirred an additional 5 min. The composition is de-aerated in a vacuum oven at 40° C. and 25 mm Hg and cast onto aluminum dishes. The samples are placed on a Carver Model 4122 pneumatic heated plate press at 165° C. Samples are allowed to heat without pressure for 10 minutes. The samples form a solid flexible disk.

EXAMPLE 49-52 AND COMPARATIVE SAMPLES 5-6

4.65 g of polycarbonate (PC) (Sabic Innovative Plastics, Lexan 121R) containing the specified amount of glycerol monostearate (GMS) (Alfa Aesar) or polybutylene terephthalate (PBT) (Sabic Innovative Plastics, Valox 310) is fed into a twin screw compounder (Haake MiniLab II, Thermo Scientific) at the specified temperature; the compounding screws are co-rotating at 100 rpm. A plasticizer prepared similarly to Examples 9-12 is added drop-wise via pipette to the melted resin in the compounder and blended for 10 minutes. This plasticizer contains 56% of species in which s is 1, v is 0 and w is 1, 25% of species in which s is 1, v is 0 and w is 2 or s is 1, v is 1 and w is 1 and 11% of species in which s is 1, v>1 and w>2. The extrudate is extruded through the die face and collected. Examples are analyzed by DSC and the results reported in Table 9. Samples of each are run according to the following profile: $1^{st}$ cycle, heat at 10° C./min from −80° C. to 200° C.; Cool at 10° C./min to −80° C.; and $2^{nd}$ cycle, heat at 10° C./min to 200° C. Tg values are calculated from the second cycle of the DSC runs.

TABLE 9

| Example | Resin | Wt % Plasticizer | Wt % GMS | Compounding Temperature (° C.) | Melt Press Temperature (° C.) | $T_g$ (° C.) |
|---|---|---|---|---|---|---|
| 49 | PC | 10 | 0.13 | 270 | 270 | 105 |
| 50 | PC | 33.8 | 0.10 | 270 | 270 | 38 |
| 51 | PBT | 10 | 0 | 230 | 235 | 10 |
| 52 | PBT | 33.3 | 0 | 230 | 235 | −66 |
| Comp. 5 | PC | 0 | 0 | 270 | 270 | 142 |
| Comp. 6 | PBT | 0 | 0 | 230 | 235 | 44 |

The present disclosure may suitably comprise, consist of, or consist essentially of, any of the disclosed or recited elements. The disclosure illustratively disclosed herein can be suitably practiced in the absence of any element which is not specifically disclosed herein. The various embodiments described above are provided by way of illustration only and should not be construed to limit the claims attached hereto. It will be recognized that various modifications and changes may be made without following the example embodiments and applications illustrated and described herein, and without departing from the true spirit and scope of the following claims.

The invention claimed is:

1. A compound having a structure corresponding to structure I

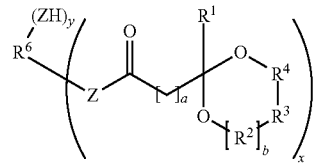

wherein
a is from 2 to 12;
b is 0 or 1;
each $R^1$ is independently hydrogen, a hydrocarbyl group, or a substituted hydrocarbyl group;
each $R^2$, $R^3$, and $R^4$ are independently methylene, alkylmethylene, or dialkylmethylene;
x is at least 1, y is 0 or a positive number and x+y is at least 2;
$R^6$ is a hydrocarbyl group or a substituted hydrocarbyl group; and
each Z is independently —O—, —NH— or —NR— where R is a hydrocarbyl group or a substituted hydrocarbyl group.

2. The compound of claim 1, wherein each Z is —O—.

3. The compound of claim 1, where y is from 0 to 2, and x is at least 2.

4. The compound of claim 1, wherein all a are 2, and all $R^1$ are methyl.

5. The compound of claim 4, where y is 0 and x is 2.

6. The compound of claim 4, wherein y is 1 and x is 1.

7. A compound of claim 1, which has the structure

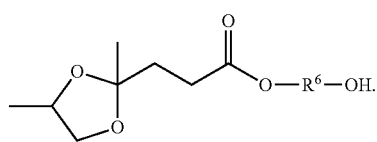

8. A compound of claim 1, which has the structure:

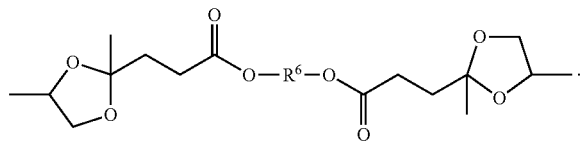

9. The compound of claim 1,
wherein
b is 1; and
x is 2.

10. A compound of claim 1, wherein $R^6$ is $C_2$-$C_6$ alkyl.

11. A mixture comprising two or more compounds, wherein each compound has a structure corresponding to structure I

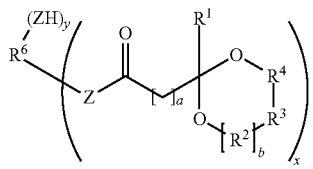

wherein
a is from 0 to 12;
b is 0 or 1;
each $R^1$ is independently hydrogen, a hydrocarbyl group, or a substituted hydrocarbyl group;
each $R^2$, $R^3$, and $R^4$ are independently methylene, alkylmethylene, or dialkylmethylene;
x is at least 1, y is 0 or a positive number and x+y is at least 2;
$R^6$ is a hydrocarbyl group or a substituted hydrocarbyl group; and
each Z is independently —O—, —NH— or —NR— where R is a hydrocarbyl group or a substituted hydrocarbyl group.

12. A composition comprising the compound of claim 1, and an organic polymer.

13. A composition comprising a mixture of claim 11, and a polymer.

14. The composition of claim 12, which has a glass transition temperature at least 5° C. lower than a glass transition temperature of the polymer.

15. The composition of claim 12, which has a glass transition temperature at least 30° C. lower than a glass transition temperature of the polymer.

16. The composition of claim 12, wherein the compound constitutes from 0.1 to 90% of the combined weight of the compound and the polymer.

17. The composition of claim 12, wherein the polymer is a thermoplastic.

18. The composition of claim 12, wherein the polymer is a thermoset.

19. The composition of claim 12, wherein the polymer comprises a poly(vinyl chloride), polyhydroxyalkanoate, a poly(lactic acid), a polystyrene, a polyurethane, a polyurea, a polyurea-urethane, a polycarbonate, an acrylic polymer, a styrene-acrylic polymer, a vinyl-acrylic polymer, an ethylene-vinyl acetate polymer, a polyester, a polyamide, a polyether, a polybutadiene, an acrylonitrile-butadiene-styrene copolymer, a styrene-butadiene-styrene copolymer, a polyvinyl acetate, an elastomer, or homopolymers thereof, or random, graft, or block copolymers thereof, or blends or mixtures thereof.

20. The composition of claim 12, wherein the composition forms a dispersed phase in a latex, a dispersion, or an emulsion.

21. The composition of claim 12, wherein the compound is melt blended or solution blended with the polymer.

22. The composition of claim 12, wherein the composition is a plastisol.

23. The composition of claim 22, wherein at least a portion of the compound is in a liquid phase of the plastisol.

24. The composition of claim 12, further comprising one or more crosslinkers, adjuvants, colorants, antifouling agents, tougheners, solvents, fillers, metal particulates, odor scavenging agents, lubricants, thermal stabilizers, light stabilizers including UV stabilizers, flame retardant additives, pigments, blowing agents, processing aids, impact modifiers, coalescing solvents, antioxidant or a combination of any two or more thereof.

25. The composition of claim 12, further comprising one or more additives selected from the group consisting of dialkyl phthalates, trimethyl pentanyl diisobutyrate, dialkyl isophthalates, dialkyl terephthalates, alkyl benzyl phthalates, dialkyl adipates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, epoxidized soybean oil, and mixtures thereof.

26. An article comprising the composition of claim 12.

27. A process for plasticizing a polymer comprising melt or solution blending a polymer and a plasticizing amount of at least one compound of claim 1.

28. The process of claim 27, wherein compound constitutes from 0.1 to 90% of the combined weights of the at least one compound and the polymer.

29. A method for making an ester or amide compound according to claim 1 comprising:
 a. contacting reagents comprising (A) one or more alkylketal esters having the structure

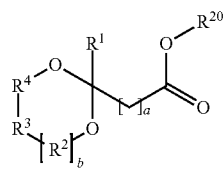

(B) a catalyst and (C) a polyol having the structure $R^6(OH)_t$ or a polyamine having the structure $R^6(NRH)_t$ or $R^6(NH_2)_t$ where R is a hydrocarbyl or substituted hydrocarbyl group and
 b. effecting a reaction to form an alcohol and a compound of claim 1, wherein t=x+y and $R^{20}$ is a hydrocarbyl group or substituted hydrocarbyl group having up to 36 carbon atoms.

30. The method of claim 29, wherein reagent (C) is a polyol having the structure $R^6(OH)_t$.

31. The method of claim 30, wherein t is 2 and the mole ratio of the alkyl ketal ester to the polyol is in a range of 2:1 to 10:1.

32. A method of making a compound of claim 1 comprising:

a. reacting a compound comprising a structure corresponding to

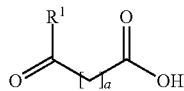

with a polyol comprising a structure corresponding to $R^6(OH)_t$ to form water and a compound comprising a structure corresponding to

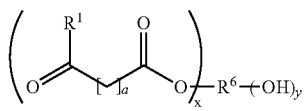

b. adding a compound comprising a structure corresponding to

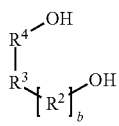

and c. effecting a reaction to form water and a compound having a structure corresponding to claim 1, wherein a, b, $R^1$, $R^2$, $R^3$, $R^4$ and $R^6$ are as defined in claim 1, x is at least 1, y is zero or a positive number and t=x+y.

33. A lubricant composition comprising an antioxidant and at least one compound having a structure corresponding to structure I

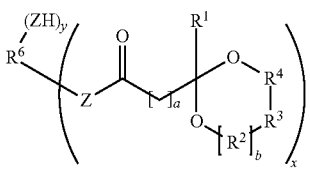

wherein
a is from 0 to 12;
b is 0 or 1;
each $R^1$ is independently hydrogen, a hydrocarbyl group, or a substituted hydrocarbyl group;
each $R^2$, $R^3$, and $R^4$ are independently methylene, alkylmethylene, or dialkylmethylene;
x is at least 1, y is 0 or a positive number and x+y is at least 2;
$R^6$ is a hydrocarbyl group or a substituted hydrocarbyl group; and
each Z is independently —O—, —NH— or —NR— where R is a hydrocarbyl group or a substituted hydrocarbyl group.

34. A method of lubricating at least two contacting surfaces, the method comprising introducing the lubricant composition of claim 33 between the two contacting surfaces.

35. The composition of claim 13, which has a glass transition temperature at least 5° C. lower than a glass transition temperature of the polymer.

36. The composition of claim 13, which has a glass transition temperature at least 30° C. lower than a glass transition temperature of the polymer.

37. The composition of claim 13, wherein the mixture constitutes from 0.1 to 90% of the combined weight of the mixture and the polymer.

38. The composition of claim 13, wherein the polymer is a thermoplastic.

39. The composition of claim 13, wherein the polymer is a thermoset.

40. The composition of claim 13, wherein the polymer comprises a poly(vinyl chloride), polyhydroxyalkanoate, a poly(lactic acid), a polystyrene, a polyurethane, a polyurea, a polyurea-urethane, a polycarbonate, an acrylic polymer, a styrene-acrylic polymer, a vinyl-acrylic polymer, an ethylene-vinyl acetate polymer, a polyester, a polyamide, a polyether, a polybutadiene, an acrylonitrile-butadiene-styrene copolymer, a styrene-butadiene-styrene copolymer, a polyvinyl acetate, an elastomer, or homopolymers thereof, or random, graft, or block copolymers thereof, or blends or mixtures thereof.

41. The composition of claim 13, wherein the composition forms a dispersed phase in a latex, a dispersion, or an emulsion.

42. The composition of claim 13, wherein the mixture is melt blended or solution blended with the polymer.

43. The composition of claim 13, wherein the composition is a plastisol.

44. The composition of claim 43, wherein at least a portion of the mixture is in a liquid phase of the plastisol.

45. The composition of claim 13, further comprising one or more crosslinkers, adjuvants, colorants, antifouling agents, tougheners, solvents, fillers, metal particulates, odor scavenging agents, lubricants, thermal stabilizers, light stabilizers including UV stabilizers, flame retardant additives, pigments, blowing agents, processing aids, impact modifiers, coalescing solvents, antioxidant or a combination of any two or more thereof.

46. The composition of claim 13, further comprising one or more additives selected from the group consisting of dialkyl phthalates, trimethyl pentanyl diisobutyrate, dialkyl isophthalates, dialkyl terephthalates, alkyl benzyl phthalates, dialkyl adipates, trialkyl trimellitates, alkylyl trialkyl citrates, dialkyl azelates, dialkyl glutarates, dialkyl sebacates, dialkyl cyclohexanedicarboxylates, esters of pentaerythritol, esters of glycerol, fatty acid triglycerides, esters of fatty acids, glycol dibenzoates, epoxidized soybean oil, and mixtures thereof.

47. An article comprising the composition of claim 13.

48. The compound of claim 1, wherein Z is —O— and $R^6$ corresponds to the residue, after removal of hydroxyl groups, of a polyol having the structure $R^6(OH)_t$, where t=x+y.

49. The compound of claim 48, wherein $R^6$ contains from 2 to 24 carbon atoms.

50. The compound of claim 48, wherein $R^6$ contains from 2 to 12 carbon atoms.

51. The compound of claim 48, wherein $R^6$ contains from 2 to 6 carbon atoms.

52. The compound of claim 48, wherein the polyol is selected from the group consisting of ethane diol, 1,2-propane diol, 1,3-propane diol, 1,4-butane diol, 1,5-pentane diol, 1,6-hexane diol, 1,4-cyclohexanediol, glycerine, trimethylolpropane, trimethylolethane, pentaerythritol, erythritol, sucrose, isosorbide, sorbitol, bisphenol-A, 2,3-dibromobutene-1,4-diol, 1,4-benzene dimethanol, 1,4-benzenediol(hydroquinone), 2-butyne-1,4-diol, 3-hexyne,3-5-diol, diethylene glycol, triethylene glycol, dipropylene glycol, tripropylene glycol, poly(ethylene oxide), poly(propylene oxide), ethylene oxide-propylene oxide copolymers and polymers of tetramethylene glycol.

53. The compound of claim 52, wherein the polyol is 1,4-butane diol.

54. The compound of claim 52, wherein the polyol is diethylene glycol.

55. A composition comprising the compound of claim 48, wherein the composition is a plastisol.

* * * * *